US007410781B2

(12) United States Patent
Karow et al.

(10) Patent No.: US 7,410,781 B2
(45) Date of Patent: Aug. 12, 2008

(54) IL-4/IL-13 SPECIFIC POLYPEPTIDES AND THERAPEUTIC USES THEREOF

(75) Inventors: Margaret Karow, Putnam Valley, NY (US); Jeanette Fairhurst, White Plains, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 525 days.

(21) Appl. No.: 11/067,251

(22) Filed: Feb. 25, 2005

(65) Prior Publication Data

US 2005/0191730 A1 Sep. 1, 2005

Related U.S. Application Data

(60) Provisional application No. 60/628,343, filed on Nov. 16, 2004, provisional application No. 60/602,139, filed on Aug. 17, 2004, provisional application No. 60/548,541, filed on Feb. 27, 2004.

(51) Int. Cl.

| | |
|---|---|
| ***C12P 21/06*** | (2006.01) |
| ***C12P 21/08*** | (2006.01) |
| ***C07H 21/04*** | (2006.01) |
| ***C12N 15/00*** | (2006.01) |
| ***C12N 1/20*** | (2006.01) |
| ***C07K 1/00*** | (2006.01) |
| ***A61K 39/00*** | (2006.01) |

(52) U.S. Cl. .................... 435/69.7; 536/23.5; 536/23.4; 435/320.1; 435/252.3; 435/325; 435/328; 435/335; 530/350; 530/388.22; 424/179.1

(58) Field of Classification Search ....................... None
See application file for complete search history.

(56) References Cited

U.S. PATENT DOCUMENTS

| | | | |
|---|---|---|---|
| 5,856,296 | A | 1/1999 | Mosley et al. |
| 6,472,179 | B2 | 10/2002 | Stahl et al. |
| 2002/0012962 | A1 | 1/2002 | Carpenter et al. |
| 2003/0143697 | A1 | 7/2003 | Stahl et al. |
| 2003/0211104 | A1 | 11/2003 | Furfine et al. |

FOREIGN PATENT DOCUMENTS

| | | |
|---|---|---|
| EP | 1 405 915 | 4/2004 |
| WO | WO 00/18932 | 4/2000 |
| WO | WO 03/092610 | 11/2003 |

OTHER PUBLICATIONS

Economides, A.N. et al., (2003) Nature Medicine 9(1):47-52.
Database EMBL 'Online! IL-4R-alpha Precursor (1992) Retrieved from EBI accession No. IL4RA_HUMAN Database Accession No. P24394.
Zhang, J.-L., et al., (2002) J. Mol. Bio. 315(3):399-407.

*Primary Examiner*—Manjunath Rao
*Assistant Examiner*—Shulamith H Shafer
(74) *Attorney, Agent, or Firm*—Valeta Gregg, Esq.; Izumi Yokoyama, Esq.

(57) ABSTRACT

Polypeptides and multimeric polypeptides capable of binding interleukin-4 (IL-4) and interleukin-13 (IL-13) which are useful therapeutically in methods of treating IL-4 and IL-13-related conditions or diseases.

27 Claims, No Drawings

SEQUENCE LISTING

```
<160> NUMBER OF SEQ ID NOS: 16

<210> SEQ ID NO 1
<211> LENGTH: 693
<212> TYPE: DNA
<213> ORGANISM: Homo sapien

<400> SEQUENCE: 1

atggtgtggc tttgctctgg gctcctgttc cctgtgagct gcctggtcct gctgcaggtg      60

gcaagctctg ggaacatgaa ggtcttgcag gagcccacct gcgtctccga ctacatgagc     120

atctctactt gcgagtggaa gatgaatggt cccaccaatt gcagcaccga gctccgcctg     180

ttgtaccagc tggtttttct gctctccgaa gcccacacgt gtatccctga gaacaacgga     240

ggcgcggggt gcgtgtgcca cctgctcatg gatgacgtgg tcagtgcgga taactataca     300

ctggacctgt gggctgggca gcagctgctg tggaagggct ccttcaagcc cagcgagcat     360

gtgaaaccca gggccccagg aaacctgaca gttcacacca atgtctccga cactctgctg     420

ctgacctgga gcaacccgta tccccctgac aattacctgt ataatcatct cacctatgca     480

gtcaacattt ggagtgaaaa cgacccggca gatttcagaa tctataacgt gacctaccta     540

gaaccctccc tccgcatcgc agccagcacc ctgaagtctg ggatttccta cagggcacgc     600

gtacgggcct gggctcagag ctataacacc acctggagtg agtggagccc cagcaccaag     660
```

-continued tggcacaact cctacaggga gcccttcgag cag 693

<210> SEQ ID NO 2
<211> LENGTH: 231
<212> TYPE: PRT
<213> ORGANISM: Homo sapien

<400> SEQUENCE: 2

Met Val Trp Leu Cys Ser Gly Leu Leu Phe Pro Val Ser Cys Leu Val
1 5 10 15

Leu Leu Gln Val Ala Ser Ser Gly Asn Met Lys Val Leu Gln Glu Pro
20 25 30

Thr Cys Val Ser Asp Tyr Met Ser Ile Ser Thr Cys Glu Trp Lys Met
35 40 45

Asn Gly Pro Thr Asn Cys Ser Thr Glu Leu Arg Leu Leu Tyr Gln Leu
50 55 60

Val Phe Leu Leu Ser Glu Ala His Thr Cys Ile Pro Glu Asn Asn Gly
65 70 75 80

Gly Ala Gly Cys Val Cys His Leu Leu Met Asp Asp Val Val Ser Ala
85 90 95

Asp Asn Tyr Thr Leu Asp Leu Trp Ala Gly Gln Gln Leu Leu Trp Lys
100 105 110

Gly Ser Phe Lys Pro Ser Glu His Val Lys Pro Arg Ala Pro Gly Asn
115 120 125

Leu Thr Val His Thr Asn Val Ser Asp Thr Leu Leu Leu Thr Trp Ser
130 135 140

Asn Pro Tyr Pro Pro Asp Asn Tyr Leu Tyr Asn His Leu Thr Tyr Ala
145 150 155 160

Val Asn Ile Trp Ser Glu Asn Asp Pro Ala Asp Phe Arg Ile Tyr Asn
165 170 175

Val Thr Tyr Leu Glu Pro Ser Leu Arg Ile Ala Ala Ser Thr Leu Lys
180 185 190

Ser Gly Ile Ser Tyr Arg Ala Arg Val Arg Ala Trp Ala Gln Cys Tyr
195 200 205

Asn Thr Thr Trp Ser Glu Trp Ser Pro Ser Thr Lys Trp His Asn Ser
210 215 220

Tyr Arg Glu Pro Phe Glu Gln
225 230

<210> SEQ ID NO 3
<211> LENGTH: 427
<212> TYPE: PRT
<213> ORGANISM: Homo sapien

<400> SEQUENCE: 3

Met Glu Trp Pro Ala Arg Leu Cys Gly Leu Trp Ala Leu Leu Leu Cys
1 5 10 15

Ala Gly Gly Gly Gly Gly Gly Gly Gly Ala Ala Pro Thr Glu Thr Gln
20 25 30

Pro Pro Val Thr Asn Leu Ser Val Ser Val Glu Asn Leu Cys Thr Val
35 40 45

Ile Trp Thr Trp Asn Pro Pro Glu Gly Ala Ser Ser Asn Cys Ser Leu
50 55 60

Trp Tyr Phe Ser His Phe Gly Asp Lys Gln Asp Lys Lys Ile Ala Pro
65 70 75 80

-continued

```
Glu Thr Arg Arg Ser Ile Glu Val Pro Leu Asn Glu Arg Ile Cys Leu
                85                  90                  95

Gln Val Gly Ser Gln Cys Ser Thr Asn Glu Ser Glu Lys Pro Ser Ile
            100                 105                 110

Leu Val Glu Lys Cys Ile Ser Pro Pro Glu Gly Asp Pro Glu Ser Ala
        115                 120                 125

Val Thr Glu Leu Gln Cys Ile Trp His Asn Leu Ser Tyr Met Lys Cys
    130                 135                 140

Ser Trp Leu Pro Gly Arg Asn Thr Ser Pro Asp Thr Asn Tyr Thr Leu
145                 150                 155                 160

Tyr Tyr Trp His Arg Ser Leu Glu Lys Ile His Gln Cys Glu Asn Ile
                165                 170                 175

Phe Arg Glu Gly Gln Tyr Phe Gly Cys Ser Phe Asp Leu Thr Lys Val
            180                 185                 190

Lys Asp Ser Ser Phe Glu Gln His Ser Val Gln Ile Met Val Lys Asp
        195                 200                 205

Asn Ala Gly Lys Ile Lys Pro Ser Phe Asn Ile Val Pro Leu Thr Ser
    210                 215                 220

Arg Val Lys Pro Asp Pro Pro His Ile Lys Asn Leu Ser Phe His Asn
225                 230                 235                 240

Asp Asp Leu Tyr Val Gln Trp Glu Asn Pro Gln Asn Phe Ile Ser Arg
                245                 250                 255

Cys Leu Phe Tyr Glu Val Glu Val Asn Asn Ser Gln Thr Glu Thr His
            260                 265                 270

Asn Val Phe Tyr Val Gln Glu Ala Lys Cys Glu Asn Pro Glu Phe Glu
        275                 280                 285

Arg Asn Val Glu Asn Thr Ser Cys Phe Met Val Pro Gly Val Leu Pro
    290                 295                 300

Asp Thr Leu Asn Thr Val Arg Ile Arg Val Lys Thr Asn Lys Leu Cys
305                 310                 315                 320

Tyr Glu Asp Asp Lys Leu Trp Ser Asn Trp Ser Gln Glu Met Ser Ile
                325                 330                 335

Gly Lys Lys Arg Asn Ser Thr Leu Tyr Ile Thr Met Leu Leu Ile Val
            340                 345                 350

Pro Val Ile Val Ala Gly Ala Ile Ile Val Leu Leu Leu Tyr Leu Lys
        355                 360                 365

Arg Leu Lys Ile Ile Ile Phe Pro Pro Ile Pro Asp Pro Gly Lys Ile
    370                 375                 380

Phe Lys Glu Met Phe Gly Asp Gln Asn Asp Asp Thr Leu His Trp Lys
385                 390                 395                 400

Lys Tyr Asp Ile Tyr Glu Lys Gln Thr Lys Glu Glu Thr Asp Ser Val
                405                 410                 415

Val Leu Ile Glu Asn Leu Lys Lys Ala Ser Gln
            420                 425


<210> SEQ ID NO 4
<211> LENGTH: 380
<212> TYPE: PRT
<213> ORGANISM: Homo sapien

<400> SEQUENCE: 4

Met Ala Phe Val Cys Leu Ala Ile Gly Cys Leu Tyr Thr Phe Leu Ile
 1               5                  10                  15

Ser Thr Thr Phe Gly Cys Thr Ser Ser Ser Asp Thr Glu Ile Lys Val
            20                  25                  30
```

-continued

```
Asn Pro Pro Gln Asp Phe Glu Ile Val Asp Pro Gly Tyr Leu Gly Tyr
        35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
        115                 120                 125

Trp Ile Ser Pro Gln Gly Ile Pro Glu Thr Lys Val Gln Asp Met Asp
    130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
    210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
        275                 280                 285

Glu Asn Glu Thr Tyr Thr Leu Lys Thr Thr Asn Glu Thr Arg Gln Leu
    290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Thr Leu Leu Arg Phe Trp Leu Pro Phe Gly Phe Ile Leu
            340                 345                 350

Ile Leu Val Ile Phe Val Thr Gly Leu Leu Leu Arg Lys Pro Asn Thr
        355                 360                 365

Tyr Pro Lys Met Ile Pro Glu Phe Phe Cys Asp Thr
    370                 375                 380


<210> SEQ ID NO 5
<211> LENGTH: 918
<212> TYPE: PRT
<213> ORGANISM: Homo sapien

<400> SEQUENCE: 5

Met Leu Thr Leu Gln Thr Trp Leu Val Gln Ala Leu Phe Ile Phe Leu
 1               5                  10                  15

Thr Thr Glu Ser Thr Gly Glu Leu Leu Asp Pro Cys Gly Tyr Ile Ser
            20                  25                  30
```

-continued

```
Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445
```

-continued

```
Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Ile Glu Ala Ile Val Val Pro
    610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
        675                 680                 685

Thr Asp Val Ser Val Val Glu Ile Glu Ala Asn Asp Lys Lys Pro Phe
    690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Ser Asp Glu Asn Glu Ser Ser Gln Asn
            740                 745                 750

Thr Ser Ser Thr Val Gln Tyr Ser Thr Val Val His Ser Gly Tyr Arg
        755                 760                 765

His Gln Val Pro Ser Val Gln Val Phe Ser Arg Ser Glu Ser Thr Gln
    770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
        835                 840                 845

Lys Gln Gln Ile Ser Asp His Ile Ser Gln Ser Cys Gly Ser Gly Gln
    850                 855                 860
```

-continued

```
Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
            900                 905                 910

Gly Gly Tyr Met Pro Gln
        915


<210> SEQ ID NO 6
<211> LENGTH: 29
<212> TYPE: PRT
<213> ORGANISM: Homo sapien

<400> SEQUENCE: 6

Met His Arg Pro Arg Arg Arg Gly Thr Arg Pro Pro Pro Leu Ala Leu
  1               5                  10                  15

Leu Ala Ala Leu Leu Leu Ala Ala Arg Gly Ala Asp Ala
             20                  25


<210> SEQ ID NO 7
<211> LENGTH: 2331
<212> TYPE: DNA
<213> ORGANISM: Homo sapien

<400> SEQUENCE: 7

atggtgtggc tttgctctgg gctcctgttc cctgtgagct gcctggtcct gctgcaggtg     60

gcaagctctg ggaacatgaa ggtcttgcag gagcccacct gcgtctccga ctacatgagc    120

atctctactt gcgagtggaa gatgaatggt cccaccaatt gcagcaccga gctccgcctg    180

ttgtaccagc tggtttttct gctctccgaa gcccacacgt gtatccctga gaacaacgga    240

ggcgcggggt gcgtgtgcca cctgctcatg gatgacgtgg tcagtgcgga taactataca    300

ctggacctgt gggctgggca gcagctgctg tggaagggct ccttcaagcc cagcgagcat    360

gtgaaaccca gggccccagg aaacctgaca gttcacacca atgtctccga cactctgctg    420

ctgacctgga gcaacccgta tccccctgac aattacctgt ataatcatct cacctatgca    480

gtcaacattt ggagtgaaaa cgacccggca gatttcagaa tctataacgt gacctaccta    540

gaaccctccc tccgcatcgc agccagcacc ctgaagtctg ggatttccta cagggcacgc    600

gtacgggcct gggctcagag ctataacacc acctggagtg agtggagccc cagcaccaag    660

tggcacaact cctacaggga gcccttcgag caggcgccta cggaaactca gccacctgtg    720

acaaatttga gtgtctctgt tgaaaacctc gcgacagtaa tatggacatg gaatccaccc    780

gagggagcca gctcaaattg tagtctatgg tattttagtc attttggcga caaacaagat    840

aagaaaatag ctccggaaac tcgtcgttca atagaagtac ccctgaatga gaggatttgt    900

ctgcaagtgg ggtcccagtg tagcaccaat gagagtgaga agcctagcat tttggttgaa    960

aaatgcatct cacccccaga aggtgatcct gagtctgctg tgactgagct tcaatgcatt   1020

tggcacaacc tgagctacat gaagtgttct tggctccctg gaaggaatac cagtcccgac   1080

actaactata ctctctacta ttggcacaga agcctggaaa aaattcatca atgtgaaaac   1140

atctttagag aaggccaata ctttggttgt tcctttgatc tgaccaaagt gaaggattcc   1200

agttttgaac aacacagtgt ccaaataatg gtcaaggata atgcaggaaa aattaaacca   1260

tccttcaata tagtgccttt aacttcccgt gtgaaacctg atcctccaca tattaaaaac   1320

ctctccttcc acaatgatga cctatatgtg caatgggaga atccacagaa ttttattagc   1380
```

-continued

```
agatgcctat tttatgaagt agaagtcaat aacagccaaa ctgagacaca taatgttttc   1440

tacgtccaag aggctaaatg tgagaatcca gaatttgaga gaaatgtgga gaatacatct   1500

tgtttcatgg tccctggtgt tcttcctgat actttgaaca cagtcagaat aagagtcaaa   1560

acaaataagt tatgctatga ggatgacaaa ctctggagta attggagcca agaaatgagt   1620

ataggtaaga agcgcaattc caccggtgac aaaactcaca catgcccacc gtgcccagca   1680

cctgaactcc tggggggacc gtcagtcttc ctcttccccc caaaacccaa ggacaccctc   1740

atgatctccc ggacccctga ggtcacatgc gtggtggtgg acgtgagcca cgaagaccct   1800

gaggtcaagt tcaactggta cgtggacggc gtggaggtgc ataatgccaa gacaaagccg   1860

cgggaggagc agtacaacag cacgtaccgt gtggtcagcg tcctcaccgt cctgcaccag   1920

gactggctga atggcaagga gtacaagtgc aaggtctcca acaaagccct cccagccccc   1980

atcgagaaaa ccatctccaa agccaaaggg cagccccgag aaccacaggt gtacaccctg   2040

cccccatccc gggatgagct gaccaagaac caggtcagcc tgacctgcct ggtcaaaggc   2100

ttctatccca gcgacatcgc cgtggagtgg gagagcaatg ggcagccgga gaacaactac   2160

aagaccacgc ctcccgtgct ggactccgac ggctccttct tcctctacag caagctcacc   2220

gtggacaaga gcaggtggca gcaggggaac gtcttctcat gctccgtgat gcatgaggct   2280

ctgcacaacc actacacgca gaagagcctc tccctgtctc cgggtaaatg a            2331
```

<210> SEQ ID NO 8
<211> LENGTH: 776
<212> TYPE: PRT
<213> ORGANISM: Homo sapien

<400> SEQUENCE: 8

```
Met Val Trp Leu Cys Ser Gly Leu Leu Phe Pro Val Ser Cys Leu Val
 1               5                  10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Ser Tyr
        195                 200                 205
```

-continued

```
Asn Thr Thr Trp Ser Glu Trp Ser Pro Ser Thr Lys Trp His Asn Ser
    210                 215                 220

Tyr Arg Glu Pro Phe Glu Gln Ala Pro Thr Glu Thr Gln Pro Pro Val
225                 230                 235                 240

Thr Asn Leu Ser Val Ser Val Glu Asn Leu Ala Thr Val Ile Trp Thr
                245                 250                 255

Trp Asn Pro Pro Glu Gly Ala Ser Ser Asn Cys Ser Leu Trp Tyr Phe
            260                 265                 270

Ser His Phe Gly Asp Lys Gln Asp Lys Lys Ile Ala Pro Glu Thr Arg
        275                 280                 285

Arg Ser Ile Glu Val Pro Leu Asn Glu Arg Ile Cys Leu Gln Val Gly
    290                 295                 300

Ser Gln Cys Ser Thr Asn Glu Ser Glu Lys Pro Ser Ile Leu Val Glu
305                 310                 315                 320

Lys Cys Ile Ser Pro Pro Glu Gly Asp Pro Glu Ser Ala Val Thr Glu
                325                 330                 335

Leu Gln Cys Ile Trp His Asn Leu Ser Tyr Met Lys Cys Ser Trp Leu
            340                 345                 350

Pro Gly Arg Asn Thr Ser Pro Asp Thr Asn Tyr Thr Leu Tyr Tyr Trp
        355                 360                 365

His Arg Ser Leu Glu Lys Ile His Gln Cys Glu Asn Ile Phe Arg Glu
    370                 375                 380

Gly Gln Tyr Phe Gly Cys Ser Phe Asp Leu Thr Lys Val Lys Asp Ser
385                 390                 395                 400

Ser Phe Glu Gln His Ser Val Gln Ile Met Val Lys Asp Asn Ala Gly
                405                 410                 415

Lys Ile Lys Pro Ser Phe Asn Ile Val Pro Leu Thr Ser Arg Val Lys
            420                 425                 430

Pro Asp Pro Pro His Ile Lys Asn Leu Ser Phe His Asn Asp Asp Leu
        435                 440                 445

Tyr Val Gln Trp Glu Asn Pro Gln Asn Phe Ile Ser Arg Cys Leu Phe
    450                 455                 460

Tyr Glu Val Glu Val Asn Asn Ser Gln Thr Glu Thr His Asn Val Phe
465                 470                 475                 480

Tyr Val Gln Glu Ala Lys Cys Glu Asn Pro Glu Phe Glu Arg Asn Val
                485                 490                 495

Glu Asn Thr Ser Cys Phe Met Val Pro Gly Val Leu Pro Asp Thr Leu
            500                 505                 510

Asn Thr Val Arg Ile Arg Val Lys Thr Asn Lys Leu Cys Tyr Glu Asp
        515                 520                 525

Asp Lys Leu Trp Ser Asn Trp Ser Gln Glu Met Ser Ile Gly Lys Lys
    530                 535                 540

Arg Asn Ser Thr Gly Asp Lys Thr His Thr Cys Pro Pro Cys Pro Ala
545                 550                 555                 560

Pro Glu Leu Leu Gly Gly Pro Ser Val Phe Leu Phe Pro Pro Lys Pro
                565                 570                 575

Lys Asp Thr Leu Met Ile Ser Arg Thr Pro Glu Val Thr Cys Val Val
            580                 585                 590

Val Asp Val Ser His Glu Asp Pro Glu Val Lys Phe Asn Trp Tyr Val
        595                 600                 605

Asp Gly Val Glu Val His Asn Ala Lys Thr Lys Pro Arg Glu Glu Gln
    610                 615                 620
```

-continued

Tyr Asn Ser Thr Tyr Arg Val Val Ser Val Leu Thr Val Leu His Gln
625 630 635 640

Asp Trp Leu Asn Gly Lys Glu Tyr Lys Cys Lys Val Ser Asn Lys Ala
645 650 655

Leu Pro Ala Pro Ile Glu Lys Thr Ile Ser Lys Ala Lys Gly Gln Pro
660 665 670

Arg Glu Pro Gln Val Tyr Thr Leu Pro Pro Ser Arg Asp Glu Leu Thr
675 680 685

Lys Asn Gln Val Ser Leu Thr Cys Leu Val Lys Gly Phe Tyr Pro Ser
690 695 700

Asp Ile Ala Val Glu Trp Glu Ser Asn Gly Gln Pro Glu Asn Asn Tyr
705 710 715 720

Lys Thr Thr Pro Pro Val Leu Asp Ser Asp Gly Ser Phe Phe Leu Tyr
725 730 735

Ser Lys Leu Thr Val Asp Lys Ser Arg Trp Gln Gln Gly Asn Val Phe
740 745 750

Ser Cys Ser Val Met His Glu Ala Leu His Asn His Tyr Thr Gln Lys
755 760 765

Ser Leu Ser Leu Ser Pro Gly Lys
770 775

<210> SEQ ID NO 9
<211> LENGTH: 2331
<212> TYPE: DNA
<213> ORGANISM: Homo sapien

<400> SEQUENCE: 9
atggtgtggc tttgctctgg gctcctgttc cctgtgagct gcctggtcct gctgcaggtg 60
gcaagctctg ggaacatgaa ggtcttgcag gagcccacct gcgtctccga ctacatgagc 120
atctctactt gcgagtggaa gatgaatggt cccaccaatt gcagcaccga gctccgcctg 180
ttgtaccagc tggtttttta taactccgaa gcccacacgt gtatccctga gaacaacgga 240
ggcgcggggt gcgtgtgcca cctgctcatg gatgacgtgg tcagtgcgga taactataca 300
ctggacctgt gggctgggca gcagctgctg tggaagggct ccttcaagcc cagcgagcat 360
gtgaaaccca gggccccagg aaacctgaca gttcacacca atgtctccga cactctgctg 420
ctgacctgga gcaacccgta tccccctgac aattacctgt ataatcatct cacctatgca 480
gtcaacattt ggagtgaaaa cgacccggca tattccagaa tctataacgt gacctaccta 540
gaaccctccc tccgcatcgc agccagcacc ctgaagtctg ggatttccta cagggcacgc 600
gtacgggcct gggctcagag ctataacacc acctggagtg agtggagccc cagcaccaag 660
tggcacaact cctacaggga gcccttcgag caggcgccta cggaaactca gccacctgtg 720
acaaatttga gtgtctctgt tgaaaacctc gcgacagtaa tatggacatg gaatccaccc 780
gagggagcca gctcaaattg tagtctatgg tattttagtc attttggcga caaacaagat 840
aagaaaatag ctccggaaac tcgtcgttca atagaagtac ccctgaatga gaggatttgt 900
ctgcaagtgg ggtcccagtg tagcaccaat gagagtgaga agcctagcat tttggttgaa 960
aaatgcatct cacccccaga aggtgatcct gagtctgctg tgactgagct tcaatgcatt 1020
tggcacaacc tgagctacat gaagtgttct tggctccctg gaaggaatac cagtcccgac 1080
actaactata ctctctacta ttggcacaga agcctggaaa aaattcatca atgtgaaaac 1140
atctttagag aaggccaata ctttggttgt tcctttgatc tgaccaaagt gaaggattcc 1200
agttttgaac aacacagtgt ccaaataatg gtcaaggata atgcaggaaa aattaaacca 1260

-continued

```
tccttcaata tagtgccttt aacttcccgt gtgaaacctg atcctccaca tattaaaaac   1320

ctctccttcc acaatgatga cctatatgtg caatgggaga atccacagaa ttttattagc   1380

agatgcctat tttatgaagt agaagtcaat aacagccaaa ctgagacaca taatgttttc   1440

tacgtccaag aggctaaatg tgagaatcca gaatttgaga gaaatgtgga gaatacatct   1500

tgtttcatgg tccctggtgt tcttcctgat actttgaaca cagtcagaat aagagtcaaa   1560

acaaataagt tatgctatga ggatgacaaa ctctggagta attggagcca agaaatgagt   1620

ataggtaaga agcgcaattc caccggtgac aaaactcaca catgcccacc gtgcccagca   1680

cctgaactcc tggggggacc gtcagtcttc ctcttccccc caaaacccaa ggacaccctc   1740

atgatctccc ggacccctga ggtcacatgc gtggtggtgg acgtgagcca cgaagaccct   1800

gaggtcaagt tcaactggta cgtggacggc gtggaggtgc ataatgccaa gacaaagccg   1860

cgggaggagc agtacaacag cacgtaccgt gtggtcagcg tcctcaccgt cctgcaccag   1920

gactggctga atggcaagga gtacaagtgc aaggtctcca acaaagccct cccagccccc   1980

atcgagaaaa ccatctccaa agccaaaggg cagccccgag aaccacaggt gtacaccctg   2040

cccccatccc gggatgagct gaccaagaac caggtcagcc tgacctgcct ggtcaaaggc   2100

ttctatccca gcgacatcgc cgtggagtgg gagagcaatg ggcagccgga gaacaactac   2160

aagaccacgc ctcccgtgct ggactccgac ggctccttct tcctctacag caagctcacc   2220

gtggacaaga gcaggtggca gcaggggaac gtcttctcat gctccgtgat gcatgaggct   2280

ctgcacaacc actacacgca gaagagcctc tccctgtctc cgggtaaatg a            2331
```

<210> SEQ ID NO 10
<211> LENGTH: 776
<212> TYPE: PRT
<213> ORGANISM: Homo sapien

<400> SEQUENCE: 10

```
Met Val Trp Leu Cys Ser Gly Leu Leu Phe Pro Val Ser Cys Leu Val
 1               5                  10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Tyr Asn Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Tyr Ser Arg Ile Tyr Asn
                165                 170                 175

Val Thr Tyr Leu Glu Pro Ser Leu Arg Ile Ala Ala Ser Thr Leu Lys
            180                 185                 190
```

-continued

```
Ser Gly Ile Ser Tyr Arg Ala Arg Val Arg Ala Trp Ala Gln Ser Tyr
        195                 200                 205

Asn Thr Thr Trp Ser Glu Trp Ser Pro Ser Thr Lys Trp His Asn Ser
    210                 215                 220

Tyr Arg Glu Pro Phe Glu Gln Ala Pro Thr Glu Thr Gln Pro Pro Val
225                 230                 235                 240

Thr Asn Leu Ser Val Ser Val Glu Asn Leu Ala Thr Val Ile Trp Thr
                245                 250                 255

Trp Asn Pro Pro Glu Gly Ala Ser Ser Asn Cys Ser Leu Trp Tyr Phe
            260                 265                 270

Ser His Phe Gly Asp Lys Gln Asp Lys Lys Ile Ala Pro Glu Thr Arg
        275                 280                 285

Arg Ser Ile Glu Val Pro Leu Asn Glu Arg Ile Cys Leu Gln Val Gly
    290                 295                 300

Ser Gln Cys Ser Thr Asn Glu Ser Glu Lys Pro Ser Ile Leu Val Glu
305                 310                 315                 320

Lys Cys Ile Ser Pro Pro Glu Gly Asp Pro Glu Ser Ala Val Thr Glu
                325                 330                 335

Leu Gln Cys Ile Trp His Asn Leu Ser Tyr Met Lys Cys Ser Trp Leu
            340                 345                 350

Pro Gly Arg Asn Thr Ser Pro Asp Thr Asn Tyr Thr Leu Tyr Tyr Trp
        355                 360                 365

His Arg Ser Leu Glu Lys Ile His Gln Cys Glu Asn Ile Phe Arg Glu
    370                 375                 380

Gly Gln Tyr Phe Gly Cys Ser Phe Asp Leu Thr Lys Val Lys Asp Ser
385                 390                 395                 400

Ser Phe Glu Gln His Ser Val Gln Ile Met Val Lys Asp Asn Ala Gly
                405                 410                 415

Lys Ile Lys Pro Ser Phe Asn Ile Val Pro Leu Thr Ser Arg Val Lys
            420                 425                 430

Pro Asp Pro Pro His Ile Lys Asn Leu Ser Phe His Asn Asp Asp Leu
        435                 440                 445

Tyr Val Gln Trp Glu Asn Pro Gln Asn Phe Ile Ser Arg Cys Leu Phe
    450                 455                 460

Tyr Glu Val Glu Val Asn Asn Ser Gln Thr Glu Thr His Asn Val Phe
465                 470                 475                 480

Tyr Val Gln Glu Ala Lys Cys Glu Asn Pro Glu Phe Glu Arg Asn Val
                485                 490                 495

Glu Asn Thr Ser Cys Phe Met Val Pro Gly Val Leu Pro Asp Thr Leu
            500                 505                 510

Asn Thr Val Arg Ile Arg Val Lys Thr Asn Lys Leu Cys Tyr Glu Asp
        515                 520                 525

Asp Lys Leu Trp Ser Asn Trp Ser Gln Glu Met Ser Ile Gly Lys Lys
    530                 535                 540

Arg Asn Ser Thr Gly Asp Lys Thr His Thr Cys Pro Pro Cys Pro Ala
545                 550                 555                 560

Pro Glu Leu Leu Gly Gly Pro Ser Val Phe Leu Phe Pro Pro Lys Pro
                565                 570                 575

Lys Asp Thr Leu Met Ile Ser Arg Thr Pro Glu Val Thr Cys Val Val
            580                 585                 590

Val Asp Val Ser His Glu Asp Pro Glu Val Lys Phe Asn Trp Tyr Val
        595                 600                 605
```

-continued

```
Asp Gly Val Glu Val His Asn Ala Lys Thr Lys Pro Arg Glu Glu Gln
    610                 615                 620

Tyr Asn Ser Thr Tyr Arg Val Val Ser Val Leu Thr Val Leu His Gln
625                 630                 635                 640

Asp Trp Leu Asn Gly Lys Glu Tyr Lys Cys Lys Val Ser Asn Lys Ala
                645                 650                 655

Leu Pro Ala Pro Ile Glu Lys Thr Ile Ser Lys Ala Lys Gly Gln Pro
            660                 665                 670

Arg Glu Pro Gln Val Tyr Thr Leu Pro Pro Ser Arg Asp Glu Leu Thr
        675                 680                 685

Lys Asn Gln Val Ser Leu Thr Cys Leu Val Lys Gly Phe Tyr Pro Ser
    690                 695                 700

Asp Ile Ala Val Glu Trp Glu Ser Asn Gly Gln Pro Glu Asn Asn Tyr
705                 710                 715                 720

Lys Thr Thr Pro Pro Val Leu Asp Ser Asp Gly Ser Phe Phe Leu Tyr
                725                 730                 735

Ser Lys Leu Thr Val Asp Lys Ser Arg Trp Gln Gln Gly Asn Val Phe
            740                 745                 750

Ser Cys Ser Val Met His Glu Ala Leu His Asn His Tyr Thr Gln Lys
        755                 760                 765

Ser Leu Ser Leu Ser Pro Gly Lys
    770                 775


<210> SEQ ID NO 11
<211> LENGTH: 2331
<212> TYPE: DNA
<213> ORGANISM: Homo sapien

<400> SEQUENCE: 11

atggtgtggc tttgctctgg gctcctgttc cctgtgagct gcctggtcct gctgcaggtg      60

gcaagctctg ggaacatgaa ggtcttgcag gagcccacct gcgtctccga ctacatgagc     120

atctctactt gcgagtggaa gatgaatggt cccaccaatt gcagcaccga gctccgcctg     180

ttgtaccagc tggtttttta taactccgaa gcccacacgt gtatccctga gaacaacgga     240

ggcgcggggt gcgtgtgcca cctgctcatg gatgacgtgg tcagtgcgga taactataca     300

ctggacctgt gggctgggca gcagctgctg tggaagggct ccttcaagcc cagcgagcat     360

gtgaaaccca gggccccagg aaacctgaca gttcacacca atgtctccga cactctgctg     420

ctgacctgga gcaacccgta tccccctgac aatttccttt ataatcatct cacctatgca     480

gtcaacattt ggagtgaaaa cgacccggca tattccagaa tctataacgt gacctaccta     540

gaaccctccc tccgcatcgc agccagcacc ctgaagtctg ggatttccta cagggcacgc     600

gtacgggcct gggctcagag ctataacacc acctggagtg agtggagccc cagcaccaag     660

tggcacaact cctacaggga gcccttcgag caggcgccta cggaaactca gccacctgtg     720

acaaatttga gtgtctctgt tgaaaacctc gcgacagtaa tatggacatg gaatccaccc     780

gagggagcca gctcaaattg tagtctatgg tattttagtc attttggcga caaacaagat     840

aagaaaatag ctccggaaac tcgtcgttca atagaagtac ccctgaatga gaggatttgt     900

ctgcaagtgg ggtcccagtg tagcaccaat gagagtgaga agcctagcat tttggttgaa     960

aaatgcatct cacccccaga aggtgatcct gagtctgctg tgactgagct tcaatgcatt    1020

tggcacaacc tgagctacat gaagtgttct tggctccctg gaaggaatac cagtcccgac    1080

actaactata ctctctacta ttggcacaga agcctggaaa aaattcatca atgtgaaaac    1140
```

-continued

```
atctttagag aaggccaata ctttggttgt tcctttgatc tgaccaaagt gaaggattcc   1200

agttttgaac aacacagtgt ccaaataatg gtcaaggata atgcaggaaa aattaaacca   1260

tccttcaata tagtgccttt aacttcccgt gtgaaacctg atcctccaca tattaaaaac   1320

ctctccttcc acaatgatga cctatatgtg caatgggaga atccacagaa ttttattagc   1380

agatgcctat tttatgaagt agaagtcaat aacagccaaa ctgagacaca taatgttttc   1440

tacgtccaag aggctaaatg tgagaatcca gaatttgaga gaaatgtgga gaatacatct   1500

tgtttcatgg tccctggtgt tcttcctgat actttgaaca cagtcagaat aagagtcaaa   1560

acaaataagt tatgctatga ggatgacaaa ctctggagta attggagcca agaaatgagt   1620

ataggtaaga agcgcaattc caccggtgac aaaactcaca catgcccacc gtgcccagca   1680

cctgaactcc tggggggacc gtcagtcttc ctcttccccc caaaacccaa ggacaccctc   1740

atgatctccc ggacccctga ggtcacatgc gtggtggtgg acgtgagcca cgaagaccct   1800

gaggtcaagt tcaactggta cgtggacggc gtggaggtgc ataatgccaa gacaaagccg   1860

cgggaggagc agtacaacag cacgtaccgt gtggtcagcg tcctcaccgt cctgcaccag   1920

gactggctga atggcaagga gtacaagtgc aaggtctcca acaaagccct cccagccccc   1980

atcgagaaaa ccatctccaa agccaaaggg cagccccgag aaccacaggt gtacaccctg   2040

cccccatccc gggatgagct gaccaagaac caggtcagcc tgacctgcct ggtcaaaggc   2100

ttctatccca gcgacatcgc cgtggagtgg gagagcaatg ggcagccgga gaacaactac   2160

aagaccacgc ctcccgtgct ggactccgac ggctccttct tcctctacag caagctcacc   2220

gtggacaaga gcaggtggca gcaggggaac gtcttctcat gctccgtgat gcatgaggct   2280

ctgcacaacc actacacgca gaagagcctc tccctgtctc cgggtaaatg a            2331
```

<210> SEQ ID NO 12
<211> LENGTH: 776
<212> TYPE: PRT
<213> ORGANISM: Homo sapien

<400> SEQUENCE: 12

```
Met Val Trp Leu Cys Ser Gly Leu Leu Phe Pro Val Ser Cys Leu Val
 1               5                  10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Tyr Asn Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140

Asn Pro Tyr Pro Pro Asp Asn Phe Leu Tyr Asn His Leu Thr Tyr Ala
145                 150                 155                 160
```

-continued

```
Val Asn Ile Trp Ser Glu Asn Asp Pro Ala Tyr Ser Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Ser Tyr
        195                 200                 205

Asn Thr Thr Trp Ser Glu Trp Ser Pro Ser Thr Lys Trp His Asn Ser
    210                 215                 220

Tyr Arg Glu Pro Phe Glu Gln Ala Pro Thr Glu Thr Gln Pro Pro Val
225                 230                 235                 240

Thr Asn Leu Ser Val Ser Val Glu Asn Leu Ala Thr Val Ile Trp Thr
                245                 250                 255

Trp Asn Pro Pro Glu Gly Ala Ser Ser Asn Cys Ser Leu Trp Tyr Phe
            260                 265                 270

Ser His Phe Gly Asp Lys Gln Asp Lys Lys Ile Ala Pro Glu Thr Arg
        275                 280                 285

Arg Ser Ile Glu Val Pro Leu Asn Glu Arg Ile Cys Leu Gln Val Gly
    290                 295                 300

Ser Gln Cys Ser Thr Asn Glu Ser Glu Lys Pro Ser Ile Leu Val Glu
305                 310                 315                 320

Lys Cys Ile Ser Pro Pro Glu Gly Asp Pro Glu Ser Ala Val Thr Glu
                325                 330                 335

Leu Gln Cys Ile Trp His Asn Leu Ser Tyr Met Lys Cys Ser Trp Leu
            340                 345                 350

Pro Gly Arg Asn Thr Ser Pro Asp Thr Asn Tyr Thr Leu Tyr Tyr Trp
        355                 360                 365

His Arg Ser Leu Glu Lys Ile His Gln Cys Glu Asn Ile Phe Arg Glu
    370                 375                 380

Gly Gln Tyr Phe Gly Cys Ser Phe Asp Leu Thr Lys Val Lys Asp Ser
385                 390                 395                 400

Ser Phe Glu Gln His Ser Val Gln Ile Met Val Lys Asp Asn Ala Gly
                405                 410                 415

Lys Ile Lys Pro Ser Phe Asn Ile Val Pro Leu Thr Ser Arg Val Lys
            420                 425                 430

Pro Asp Pro Pro His Ile Lys Asn Leu Ser Phe His Asn Asp Asp Leu
        435                 440                 445

Tyr Val Gln Trp Glu Asn Pro Gln Asn Phe Ile Ser Arg Cys Leu Phe
    450                 455                 460

Tyr Glu Val Glu Val Asn Asn Ser Gln Thr Glu Thr His Asn Val Phe
465                 470                 475                 480

Tyr Val Gln Glu Ala Lys Cys Glu Asn Pro Glu Phe Glu Arg Asn Val
                485                 490                 495

Glu Asn Thr Ser Cys Phe Met Val Pro Gly Val Leu Pro Asp Thr Leu
            500                 505                 510

Asn Thr Val Arg Ile Arg Val Lys Thr Asn Lys Leu Cys Tyr Glu Asp
        515                 520                 525

Asp Lys Leu Trp Ser Asn Trp Ser Gln Glu Met Ser Ile Gly Lys Lys
    530                 535                 540

Arg Asn Ser Thr Gly Asp Lys Thr His Thr Cys Pro Pro Cys Pro Ala
545                 550                 555                 560

Pro Glu Leu Leu Gly Gly Pro Ser Val Phe Leu Phe Pro Pro Lys Pro
                565                 570                 575
```

-continued

```
Lys Asp Thr Leu Met Ile Ser Arg Thr Pro Glu Val Thr Cys Val Val
            580                 585                 590

Val Asp Val Ser His Glu Asp Pro Glu Val Lys Phe Asn Trp Tyr Val
        595                 600                 605

Asp Gly Val Glu Val His Asn Ala Lys Thr Lys Pro Arg Glu Glu Gln
    610                 615                 620

Tyr Asn Ser Thr Tyr Arg Val Val Ser Val Leu Thr Val Leu His Gln
625                 630                 635                 640

Asp Trp Leu Asn Gly Lys Glu Tyr Lys Cys Lys Val Ser Asn Lys Ala
                645                 650                 655

Leu Pro Ala Pro Ile Glu Lys Thr Ile Ser Lys Ala Lys Gly Gln Pro
            660                 665                 670

Arg Glu Pro Gln Val Tyr Thr Leu Pro Pro Ser Arg Asp Glu Leu Thr
        675                 680                 685

Lys Asn Gln Val Ser Leu Thr Cys Leu Val Lys Gly Phe Tyr Pro Ser
    690                 695                 700

Asp Ile Ala Val Glu Trp Glu Ser Asn Gly Gln Pro Glu Asn Asn Tyr
705                 710                 715                 720

Lys Thr Thr Pro Pro Val Leu Asp Ser Asp Gly Ser Phe Phe Leu Tyr
                725                 730                 735

Ser Lys Leu Thr Val Asp Lys Ser Arg Trp Gln Gln Gly Asn Val Phe
            740                 745                 750

Ser Cys Ser Val Met His Glu Ala Leu His Asn His Tyr Thr Gln Lys
        755                 760                 765

Ser Leu Ser Leu Ser Pro Gly Lys
    770                 775


<210> SEQ ID NO 13
<211> LENGTH: 2331
<212> TYPE: DNA
<213> ORGANISM: Homo sapien

<400> SEQUENCE: 13

atggtgtggc tttgctctgg gctcctgttc cctgtgagct gcctggtcct gctgcaggtg      60

gcaagctctg ggaacatgaa ggtcttgcag gagcccacct gcgtctccga ctacatgagc     120

atctctactt gcgagtggaa gatgaatggt cccaccaatt gcagcaccga gctccgcctg     180

ttgtaccagc tggtttttta taactccgaa gcccacacgt gtatccctga gaacaacgga     240

ggcgcggggt gcgtgtgcca cctgctcatg gatgacgtgg tcagtgcgga taactataca     300

ctggacctgt gggctgggca gcagctgctg tggaagggct ccttcaagcc cagcgagcat     360

gtgaaaccca gggccccagg aaacctgaca gttcacacca atgtctccga cactctgctg     420

ctgacctgga gcaacccgta tccccctgac aattacctgt ataatcatct cacctatgca     480

gtcaacattt ggagtgaaaa cgacccggca ttttctagaa tctataacgt gacctaccta     540

gaaccctccc tccgcatcgc agccagcacc ctgaagtctg ggatttccta cagggcacgc     600

gtacgggcct gggctcagag ctataacacc acctggagtg agtggagccc cagcaccaag     660

tggcacaact cctacaggga gcccttcgag caggcgccta cggaaactca gccacctgtg     720

acaaatttga gtgtctctgt tgaaaacctc gcgacagtaa tatggacatg gaatccaccc     780

gagggagcca gctcaaattg tagtctatgg tattttagtc attttggcga caaacaagat     840

aagaaaatag ctccggaaac tcgtcgttca atagaagtac ccctgaatga gaggatttgt     900

ctgcaagtgg ggtcccagtg tagcaccaat gagagtgaga agcctagcat tttggttgaa     960
```

-continued

```
aaatgcatct cacccccaga aggtgatcct gagtctgctg tgactgagct tcaatgcatt   1020

tggcacaacc tgagctacat gaagtgttct tggctccctg gaaggaatac cagtcccgac   1080

actaactata ctctctacta ttggcacaga agcctggaaa aaattcatca atgtgaaaac   1140

atctttagag aaggccaata ctttggttgt tcctttgatc tgaccaaagt gaaggattcc   1200

agttttgaac aacacagtgt ccaaataatg gtcaaggata atgcaggaaa aattaaacca   1260

tccttcaata tagtgccttt aacttcccgt gtgaaacctg atcctccaca tattaaaaac   1320

ctctccttcc acaatgatga cctatatgtg caatgggaga atccacagaa ttttattagc   1380

agatgcctat tttatgaagt agaagtcaat aacagccaaa ctgagacaca taatgttttc   1440

tacgtccaag aggctaaatg tgagaatcca gaatttgaga gaaatgtgga gaatacatct   1500

tgtttcatgg tccctggtgt tcttcctgat actttgaaca cagtcagaat aagagtcaaa   1560

acaaataagt tatgctatga ggatgacaaa ctctggagta attggagcca agaaatgagt   1620

ataggtaaga agcgcaattc caccggtgac aaaactcaca catgcccacc gtgcccagca   1680

cctgaactcc tggggggacc gtcagtcttc ctcttccccc caaaacccaa ggacaccctc   1740

atgatctccc ggacccctga ggtcacatgc gtggtggtgg acgtgagcca cgaagaccct   1800

gaggtcaagt tcaactggta cgtggacggc gtggaggtgc ataatgccaa gacaaagccg   1860

cgggaggagc agtacaacag cacgtaccgt gtggtcagcg tcctcaccgt cctgcaccag   1920

gactggctga atggcaagga gtacaagtgc aaggtctcca acaaagccct cccagccccc   1980

atcgagaaaa ccatctccaa agccaaaggg cagccccgag aaccacaggt gtacaccctg   2040

cccccatccc gggatgagct gaccaagaac caggtcagcc tgacctgcct ggtcaaaggc   2100

ttctatccca gcgacatcgc cgtggagtgg gagagcaatg ggcagccgga gaacaactac   2160

aagaccacgc ctcccgtgct ggactccgac ggctccttct tcctctacag caagctcacc   2220

gtggacaaga gcaggtggca gcaggggaac gtcttctcat gctccgtgat gcatgaggct   2280

ctgcacaacc actacacgca gaagagcctc tccctgtctc cgggtaaatg a            2331
```

<210> SEQ ID NO 14
<211> LENGTH: 776
<212> TYPE: PRT
<213> ORGANISM: Homo sapien

<400> SEQUENCE: 14

```
Met Val Trp Leu Cys Ser Gly Leu Leu Phe Pro Val Ser Cys Leu Val
 1               5                  10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Tyr Asn Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125
```

-continued

```
Leu Thr Val His Thr Asn Val Ser Asp Thr Leu Leu Leu Thr Trp Ser
    130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Phe Ser Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Ser Tyr
        195                 200                 205

Asn Thr Thr Trp Ser Glu Trp Ser Pro Ser Thr Lys Trp His Asn Ser
    210                 215                 220

Tyr Arg Glu Pro Phe Glu Gln Ala Pro Thr Glu Thr Gln Pro Pro Val
225                 230                 235                 240

Thr Asn Leu Ser Val Ser Val Glu Asn Leu Ala Thr Val Ile Trp Thr
                245                 250                 255

Trp Asn Pro Pro Glu Gly Ala Ser Ser Asn Cys Ser Leu Trp Tyr Phe
            260                 265                 270

Ser His Phe Gly Asp Lys Gln Asp Lys Lys Ile Ala Pro Glu Thr Arg
        275                 280                 285

Arg Ser Ile Glu Val Pro Leu Asn Glu Arg Ile Cys Leu Gln Val Gly
    290                 295                 300

Ser Gln Cys Ser Thr Asn Glu Ser Glu Lys Pro Ser Ile Leu Val Glu
305                 310                 315                 320

Lys Cys Ile Ser Pro Pro Glu Gly Asp Pro Glu Ser Ala Val Thr Glu
                325                 330                 335

Leu Gln Cys Ile Trp His Asn Leu Ser Tyr Met Lys Cys Ser Trp Leu
            340                 345                 350

Pro Gly Arg Asn Thr Ser Pro Asp Thr Asn Tyr Thr Leu Tyr Tyr Trp
        355                 360                 365

His Arg Ser Leu Glu Lys Ile His Gln Cys Glu Asn Ile Phe Arg Glu
    370                 375                 380

Gly Gln Tyr Phe Gly Cys Ser Phe Asp Leu Thr Lys Val Lys Asp Ser
385                 390                 395                 400

Ser Phe Glu Gln His Ser Val Gln Ile Met Val Lys Asp Asn Ala Gly
                405                 410                 415

Lys Ile Lys Pro Ser Phe Asn Ile Val Pro Leu Thr Ser Arg Val Lys
            420                 425                 430

Pro Asp Pro Pro His Ile Lys Asn Leu Ser Phe His Asn Asp Asp Leu
        435                 440                 445

Tyr Val Gln Trp Glu Asn Pro Gln Asn Phe Ile Ser Arg Cys Leu Phe
    450                 455                 460

Tyr Glu Val Glu Val Asn Asn Ser Gln Thr Glu Thr His Asn Val Phe
465                 470                 475                 480

Tyr Val Gln Glu Ala Lys Cys Glu Asn Pro Glu Phe Glu Arg Asn Val
                485                 490                 495

Glu Asn Thr Ser Cys Phe Met Val Pro Gly Val Leu Pro Asp Thr Leu
            500                 505                 510

Asn Thr Val Arg Ile Arg Val Lys Thr Asn Lys Leu Cys Tyr Glu Asp
        515                 520                 525

Asp Lys Leu Trp Ser Asn Trp Ser Gln Glu Met Ser Ile Gly Lys Lys
    530                 535                 540
```

-continued

```
Arg Asn Ser Thr Gly Asp Lys Thr His Thr Cys Pro Pro Cys Pro Ala
545                 550                 555                 560

Pro Glu Leu Leu Gly Gly Pro Ser Val Phe Leu Phe Pro Pro Lys Pro
                565                 570                 575

Lys Asp Thr Leu Met Ile Ser Arg Thr Pro Glu Val Thr Cys Val Val
            580                 585                 590

Val Asp Val Ser His Glu Asp Pro Glu Val Lys Phe Asn Trp Tyr Val
        595                 600                 605

Asp Gly Val Glu Val His Asn Ala Lys Thr Lys Pro Arg Glu Glu Gln
    610                 615                 620

Tyr Asn Ser Thr Tyr Arg Val Val Ser Val Leu Thr Val Leu His Gln
625                 630                 635                 640

Asp Trp Leu Asn Gly Lys Glu Tyr Lys Cys Lys Val Ser Asn Lys Ala
                645                 650                 655

Leu Pro Ala Pro Ile Glu Lys Thr Ile Ser Lys Ala Lys Gly Gln Pro
            660                 665                 670

Arg Glu Pro Gln Val Tyr Thr Leu Pro Pro Ser Arg Asp Glu Leu Thr
        675                 680                 685

Lys Asn Gln Val Ser Leu Thr Cys Leu Val Lys Gly Phe Tyr Pro Ser
    690                 695                 700

Asp Ile Ala Val Glu Trp Glu Ser Asn Gly Gln Pro Glu Asn Asn Tyr
705                 710                 715                 720

Lys Thr Thr Pro Pro Val Leu Asp Ser Asp Gly Ser Phe Phe Leu Tyr
                725                 730                 735

Ser Lys Leu Thr Val Asp Lys Ser Arg Trp Gln Gln Gly Asn Val Phe
            740                 745                 750

Ser Cys Ser Val Met His Glu Ala Leu His Asn His Tyr Thr Gln Lys
        755                 760                 765

Ser Leu Ser Leu Ser Pro Gly Lys
    770                 775
```

<210> SEQ ID NO 15
<211> LENGTH: 2331
<212> TYPE: DNA
<213> ORGANISM: Homo sapien

<400> SEQUENCE: 15

```
atggtgtggc tttgctctgg gctcctgttc cctgtgagct gcctggtcct gctgcaggtg      60

gcaagctctg ggaacatgaa ggtcttgcag gagcccacct gcgtctccga ctacatgagc     120

atctctactt gcgagtggaa gatgaatggt cccaccaatt gcagcaccga gctccgcctg     180

ttgtaccagc tggtttttta taactccgaa gcccacacgt gtatccctga gaacaacgga     240

ggcgcggggt gcgtgtgcca cctgctcatg gatgacgtgg tcagtgcgga taactataca     300

ctggacctgt gggctgggca gcagctgctg tggaagggct ccttcaagcc cagcgagcat     360

gtgaaaccca gggccccagg aaacctgaca gttcacacca atgtctccga cactctgctg     420

ctgacctgga gcaacccgta tccccctgac aatttccttt ataatcatct cacctatgca     480

gtcaacattt ggagtgaaaa cgacccggca ttttctagaa tctataacgt gacctaccta     540

gaaccctccc tccgcatcgc agccagcacc ctgaagtctg ggatttccta cagggcacgc     600

gtacgggcct gggctcagag ctataacacc acctggagtg agtggagccc cagcaccaag     660

tggcacaact cctacaggga gcccttcgag caggcgccta cggaaactca gccacctgtg     720

acaaatttga gtgtctctgt tgaaaacctc gcgacagtaa tatggacatg gaatccaccc     780
```

-continued

```
gagggagcca gctcaaattg tagtctatgg tattttagtc attttggcga caaacaagat    840

aagaaaatag ctccggaaac tcgtcgttca atagaagtac cctgaatga gaggatttgt    900

ctgcaagtgg ggtcccagtg tagcaccaat gagagtgaga agcctagcat tttggttgaa    960

aaatgcatct cacccccaga aggtgatcct gagtctgctg tgactgagct tcaatgcatt   1020

tggcacaacc tgagctacat gaagtgttct tggctccctg gaaggaatac cagtcccgac   1080

actaactata ctctctacta ttggcacaga agcctggaaa aaattcatca atgtgaaaac   1140

atctttagag aaggccaata ctttggttgt tcctttgatc tgaccaaagt gaaggattcc   1200

agttttgaac aacacagtgt ccaaataatg gtcaaggata atgcaggaaa aattaaacca   1260

tccttcaata tagtgccttt aacttcccgt gtgaaacctg atcctccaca tattaaaaac   1320

ctctccttcc acaatgatga cctatatgtg caatgggaga atccacagaa ttttattagc   1380

agatgcctat tttatgaagt agaagtcaat aacagccaaa ctgagacaca taatgttttc   1440

tacgtccaag aggctaaatg tgagaatcca gaatttgaga gaaatgtgga gaatacatct   1500

tgtttcatgg tccctggtgt tcttcctgat actttgaaca cagtcagaat aagagtcaaa   1560

acaaataagt tatgctatga ggatgacaaa ctctggagta attggagcca agaaatgagt   1620

ataggtaaga agcgcaattc caccggtgac aaaactcaca catgcccacc gtgcccagca   1680

cctgaactcc tggggggacc gtcagtcttc ctcttccccc caaaacccaa ggacaccctc   1740

atgatctccc ggacccctga ggtcacatgc gtggtggtgg acgtgagcca cgaagaccct   1800

gaggtcaagt tcaactggta cgtggacggc gtggaggtgc ataatgccaa gacaaagccg   1860

cgggaggagc agtacaacag cacgtaccgt gtggtcagcg tcctcaccgt cctgcaccag   1920

gactggctga atggcaagga gtacaagtgc aaggtctcca acaaagccct cccagccccc   1980

atcgagaaaa ccatctccaa agccaaaggg cagccccgag aaccacaggt gtacaccctg   2040

cccccatccc gggatgagct gaccaagaac caggtcagcc tgacctgcct ggtcaaaggc   2100

ttctatccca gcgacatcgc cgtggagtgg gagagcaatg ggcagccgga gaacaactac   2160

aagaccacgc ctcccgtgct ggactccgac ggctccttct tcctctacag caagctcacc   2220

gtggacaaga gcaggtggca gcaggggaac gtcttctcat gctccgtgat gcatgaggct   2280

ctgcacaacc actacacgca gaagagcctc tccctgtctc cgggtaaatg a            2331
```

<210> SEQ ID NO 16
<211> LENGTH: 776
<212> TYPE: PRT
<213> ORGANISM: Homo sapien

<400> SEQUENCE: 16

```
Met Val Trp Leu Cys Ser Gly Leu Leu Phe Pro Val Ser Cys Leu Val
 1               5                  10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Tyr Asn Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95
```

-continued

```
Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140

Asn Pro Tyr Pro Pro Asp Asn Phe Leu Tyr Asn His Leu Thr Tyr Ala
145                 150                 155                 160

Val Asn Ile Trp Ser Glu Asn Asp Pro Ala Phe Ser Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Ser Tyr
        195                 200                 205

Asn Thr Thr Trp Ser Glu Trp Ser Pro Ser Thr Lys Trp His Asn Ser
    210                 215                 220

Tyr Arg Glu Pro Phe Glu Gln Ala Pro Thr Glu Thr Gln Pro Pro Val
225                 230                 235                 240

Thr Asn Leu Ser Val Ser Val Glu Asn Leu Ala Thr Val Ile Trp Thr
                245                 250                 255

Trp Asn Pro Pro Glu Gly Ala Ser Ser Asn Cys Ser Leu Trp Tyr Phe
            260                 265                 270

Ser His Phe Gly Asp Lys Gln Asp Lys Lys Ile Ala Pro Glu Thr Arg
        275                 280                 285

Arg Ser Ile Glu Val Pro Leu Asn Glu Arg Ile Cys Leu Gln Val Gly
    290                 295                 300

Ser Gln Cys Ser Thr Asn Glu Ser Glu Lys Pro Ser Ile Leu Val Glu
305                 310                 315                 320

Lys Cys Ile Ser Pro Pro Glu Gly Asp Pro Glu Ser Ala Val Thr Glu
                325                 330                 335

Leu Gln Cys Ile Trp His Asn Leu Ser Tyr Met Lys Cys Ser Trp Leu
            340                 345                 350

Pro Gly Arg Asn Thr Ser Pro Asp Thr Asn Tyr Thr Leu Tyr Tyr Trp
        355                 360                 365

His Arg Ser Leu Glu Lys Ile His Gln Cys Glu Asn Ile Phe Arg Glu
    370                 375                 380

Gly Gln Tyr Phe Gly Cys Ser Phe Asp Leu Thr Lys Val Lys Asp Ser
385                 390                 395                 400

Ser Phe Glu Gln His Ser Val Gln Ile Met Val Lys Asp Asn Ala Gly
                405                 410                 415

Lys Ile Lys Pro Ser Phe Asn Ile Val Pro Leu Thr Ser Arg Val Lys
            420                 425                 430

Pro Asp Pro Pro His Ile Lys Asn Leu Ser Phe His Asn Asp Asp Leu
        435                 440                 445

Tyr Val Gln Trp Glu Asn Pro Gln Asn Phe Ile Ser Arg Cys Leu Phe
    450                 455                 460

Tyr Glu Val Glu Val Asn Asn Ser Gln Thr Glu Thr His Asn Val Phe
465                 470                 475                 480

Tyr Val Gln Glu Ala Lys Cys Glu Asn Pro Glu Phe Glu Arg Asn Val
                485                 490                 495

Glu Asn Thr Ser Cys Phe Met Val Pro Gly Val Leu Pro Asp Thr Leu
            500                 505                 510
```

-continued

```
Asn Thr Val Arg Ile Arg Val Lys Thr Asn Lys Leu Cys Tyr Glu Asp
        515                 520                 525

Asp Lys Leu Trp Ser Asn Trp Ser Gln Glu Met Ser Ile Gly Lys Lys
    530                 535                 540

Arg Asn Ser Thr Gly Asp Lys Thr His Thr Cys Pro Pro Cys Pro Ala
545                 550                 555                 560

Pro Glu Leu Leu Gly Gly Pro Ser Val Phe Leu Phe Pro Pro Lys Pro
                565                 570                 575

Lys Asp Thr Leu Met Ile Ser Arg Thr Pro Glu Val Thr Cys Val Val
            580                 585                 590

Val Asp Val Ser His Glu Asp Pro Glu Val Lys Phe Asn Trp Tyr Val
        595                 600                 605

Asp Gly Val Glu Val His Asn Ala Lys Thr Lys Pro Arg Glu Glu Gln
    610                 615                 620

Tyr Asn Ser Thr Tyr Arg Val Val Ser Val Leu Thr Val Leu His Gln
625                 630                 635                 640

Asp Trp Leu Asn Gly Lys Glu Tyr Lys Cys Lys Val Ser Asn Lys Ala
                645                 650                 655

Leu Pro Ala Pro Ile Glu Lys Thr Ile Ser Lys Ala Lys Gly Gln Pro
            660                 665                 670

Arg Glu Pro Gln Val Tyr Thr Leu Pro Pro Ser Arg Asp Glu Leu Thr
        675                 680                 685

Lys Asn Gln Val Ser Leu Thr Cys Leu Val Lys Gly Phe Tyr Pro Ser
    690                 695                 700

Asp Ile Ala Val Glu Trp Glu Ser Asn Gly Gln Pro Glu Asn Asn Tyr
705                 710                 715                 720

Lys Thr Thr Pro Pro Val Leu Asp Ser Asp Gly Ser Phe Phe Leu Tyr
                725                 730                 735

Ser Lys Leu Thr Val Asp Lys Ser Arg Trp Gln Gln Gly Asn Val Phe
            740                 745                 750

Ser Cys Ser Val Met His Glu Ala Leu His Asn His Tyr Thr Gln Lys
        755                 760                 765

Ser Leu Ser Leu Ser Pro Gly Lys
    770                 775
```

IL-4/IL-13 SPECIFIC POLYPEPTIDES AND THERAPEUTIC USES THEREOF

CROSS-REFERENCE TO RELATED APPLICATIONS

This application claims the benefit under 35 USC § 119(e) of U.S. Provisionals 60/548,541 filed 27 Feb. 2004, 60/602,139 filed 17 Aug. 2004, and 60/628,343 filed 16 Nov. 2004, which applications are herein specifically incorporated by reference in their entirety.

BACKGROUND OF THE INVENTION

1. Field of the Invention

The invention encompasses IL-4/IL-13-specific polypeptides, as well as therapeutic uses of such polypeptides for inhibiting IL-4 and/or IL-13 activity.

2. Description of Related Art

In U.S. Pat. No. 6,472,179 Stahl et al. describe cytokine fusion protein fusion polypeptides capable of binding a cytokine to form a nonfunctional complex composed of two receptor components and a multimerizing component. The interleukin-4 receptor alpha (IL-4Rα), and the IL-13 receptor alpha component (IL-13Rα), are described, e.g., U.S. Pat. No. 5,856,296, and 5,840,869, and EP 876482, which publications are herein incorporated by reference in their entireties.

BRIEF SUMMARY OF THE INVENTION

In a first aspect, the invention features an nucleic acid molecule encoding an interleukin 4 (IL-4) and IL-13-binding fusion polypeptide $(R1)_x$-$(R2)_y$-F, wherein R1 is a modified IL-4 receptor alpha (IL-4Rα) component capable of specifically inhibiting IL-4 activity with an IC50 of at least $10^{-10}$ molar when present as a component in the fusion polypeptide, R2 is an IL-13 receptor alpha 1 or 2 (IL-13Rα1 or IL-13Rα2) capable of specifically inhibiting IL-13 activity with an IC50 of at least $10^{-10}$ molar when present as a component in the fusion polypeptide, F is a fusion component, and x and y are each independently a positive integer ≧1. The components of the fusion polypeptide may be arranged in different orders, for example, F-$(R1)_x(R2)_y$, $(R1)_x$-F-$(R2)_y$, or $(R2)_y$-F-$(R1)_x$. More specifically, R1 is derived from a parent IL-4Rα component which is amino acids 1-231, 24-231, 28-231, or 24-221 of SEQ ID NO:2, or an allelic variant thereof, with one or more modifications defined in modification group I, and R2 is an IL-13Rα1 or IL-13Rα2 component comprising 1-343 or 27-343 of SEQ ID NO:3, or a fragment thereof, optionally modified with one or more of the modifications defined in modification group II, or comprising amino acids 1-343 or 23-343 of SEQ ID NO:4, optionally modified with one or more of the modifications defined in modification group III. Optionally, $(R1)_x$-$(R2)_y$-F further comprises a signal sequence (SS). In one embodiment, the R1 component of the fusion polypeptide is modified to exhibit an increased or decreased IL-4 inhibitory activity and/or an increased or decreased IL-13 inhibitory activity relative to the unmodified component, preferably the modifications to R1 increases both IL-4 and IL-13 inhibition.

R1: The naturally occurring wild-type IL-4Rα protein is an 800 amino acid protein having the extracellular domain shown in SEQ ID NO:2 (encoded by SEQ ID NO:1). Known allelic variants of SEQ ID NO:2 include, but are not limited to, Phe, Val, or Leu at position 75 (Ile75PheNal/Leu) and/or Val131Leu. In one embodiment, R1 comprises amino acids 24-231 of SEQ ID NO:2, or an allelic variant thereof, optionally further modified by one or more modifications defined in modification group I. In another embodiment, R1 is amino acids 1-231 of SEQ ID NO:2, or an allelic variant thereof, with at least one of the modifications selected from those listed in modification group I . These modifications provide novel polypeptides with specifically desired properties, such as, for example, improved solubility, reduced immunogenicity, improved PK, improved production characteristics, and/or improved ability to block IL-4 and/or IL-13 activity.

Modification Group I: amino acid at position 67, 68, 71, 152, 164, 171, 172, 175, 198, and/or 207 of SEQ ID NO:2 is (are) replaced with a different amino acid. In preferred embodiments, the amino acid(s) substitution is (are) as follows: Leu at position 67 is replaced with Tyr (Leu67Tyr); Leu68Asn, which may remove a hydrophobic patch and may be desirable in specific situations to improve solubility and/or ability to block IL-4 and/or IL-13; Asp171Tyr/Phe; Phe172Ser, which may neutralize an acidic electropotential and decreases the size of a hydrophobic patch, thus may be desirable for improved solubility and/or folding of the fusion polypeptide; Tyr152Phe, which changes an amino acid in the ligand binding site, and thus may be desirable for improving the inhibitory activity for IL-13 and/or IL-4; Arg198Ser, which removes a positively charged patch and thus may be desirable to improve purification properties; and Cys207Ser, which decreases the formation of aberrant disulfide bonds and may thus be desirable to reduce covalent aggregation and/or incorrect disulfide bonding. Modifications which result in the addition of a glycosylation site include Ala71Asn and Trp164Ser. In some embodiments, the addition of one or more glycosylation sites is desirable to reduce immunogenicity, or increase solubility or in vivo stability relative to the same protein without additional glycosylation site(s). In preferred embodiments, R1 comprises 1-231 of SEQ ID NO:2 with Cys207Ser, further modified by changes at one or more of positions 67, 68, 152,171 and 172. In preferred embodiments, R1 comprises modifications at (i) 67, 68 and 207; (ii) 67, 68, 152 and 207; (iii) 152 and 207; (iv) 67, 171, 172 and 207; (v) 68, 171, 172, and 207; (vi) 67, 68, 171 and 207; (vii) 67, 68, 172 and 207; (viii) 152, 171, 172 and 207; (ix) 67, 68, 171, 172 and 207; (x) 67, 68, 152, 171, 172 and 207; (xi) 171, 172, and 207. In further preferred embodiments, R1 comprises Cys207Ser and a modification selected from the group consisting of (i) Leu67Tyr+Leu68Asn, (ii) Tyr152Phe, (iii) Asp171Tyr/Phe+Phe172Ser, (iv) Leu67Tyr+Leu68Asn+Tyr152Phe, (v) Tyr152Phe+Asp171Tyr/Phe+Phe172Ser, (vi) Leu67Tyr+Leu68Asn+Asp171Tyr/Phe+Phe172Ser, (vii) Tyr152Phe+Leu67Tyr+Leu68Asn+Asp171Tyr/Phe+Phe172Ser.

R2: The naturally occurring human wild-type IL-13Rα1 protein is an 427 amino acid protein having the sequence of SEQ ID NO:3 including a 343 amino acid extracellular domain. In one embodiment, R2 is an IL-13-binding polypeptide component comprising amino acids 1-343 or 27-343 of SEQ ID NO:3, optionally modified with one or more of the modifications defined in modification group II. In another embodiment, R2 is an IL-13-binding polypeptide component comprising amino acids 1-343 or 23-343 of SEQ ID NO:4, optionally modified with one or more of the modifications defined in modification group III.

Modification Group II: (a) amino acids 1-120 of SEQ ID NO:3 are replaced with amino acids 1-123 of human gp130 (SEQ ID NO:5); (b) amino acids 338-343 of SEQ ID NO:3 are deleted; (c) amino acids 1-26 of SEQ ID NO:3 are replaced with a different signal sequence, for example, SEQ ID NO:6, or (d) one or more of amino acid(s) at position 46, 73, 143, 235, 293 and/or 329 of SEQ ID NO:3 are replaced with a different amino acid. In more specific embodiments, the preferred replacement is Cys at position 46 (of SEQ ID NO:3) with any one of Ala, Gly, or Tyr (Cys46Ala/Gly/Tyr), preferably Ala, which in specific embodiments may be desirable to reduce aberrant disulfide formation and covalent aggregates; Lys73Gln; Lys143Gln, which removes highly positively charged patches and may be desirable in specific embodiments to reduce aggregation and/or increase solubility. R2 may be further modified at one or more glycosylation sites to remove sites that are incompletely glycosylated and may be desirable to improve pharmacokinetics and/or production consistency: Asn235Ser/His, Asn293Gly, Asn329Asp.

Modification Group III: (a') amino acids 1-22 of SEQ ID NO:4 are deleted. In specific embodiments in which it may be desirable to replace the deleted amino acids with, for example, a signal sequence such as SEQ ID NO:6, thus removing Cys22 to reduce aberrant disulfide bonds formation; (b') Cys252Ile of SEQ ID NO:4; (c') an amino acid changed at position 310 of SEQ ID NO:4. In a specific embodiment, Ser310 is replaced with Cys, which may be desirable to stabilize the tertiary structure of the protein.

The optional fusion component (F) is any component that enhances the functionality of the fusion polypeptide. Thus, for example, a fusion component may enhance the biological activity of the fusion polypeptide, aid in its production and/or recovery, or enhance a pharmacological property or the pharmacokinetic profile of the fusion polypeptide by, for example, enhancing its serum half-life, tissue penetrability, lack of immunogenicity, or stability. In preferred embodiments, the fusion component is selected from the group consisting of a multimerizing component, a serum protein, or a molecule capable of binding a serum protein.

When the fusion component is a multimerizing component, it includes any natural or synthetic sequence capable of interacting with another multimerizing component to form a higher order structure, e.g., a dimer, a trimer, etc. In specific embodiments, the multimerizing component is selected from the group consisting of (i) an immunoglobulin-derived domain, (ii) a cleavable region (C-region), (ii) an amino acid sequence between 1 to about 500 amino acids in length, optionally comprising at least one cysteine residue, (iii) a leucine zipper, (iv) a helix loop motif, and (v) a coil-coil motif. In a more specific embodiment, the immunoglobulin-derived domain is selected from the group consisting of the Fc domain of IgG or the heavy chain of IgG. In a most specific embodiment the Fc domain of IgG is human FcΔ1(a), an Fc molecule with a deletion of the region involved in forming the disulfide bond with the light chain.

When the fusion component is a serum protein, the serum protein may be any serum protein or a fragment of a serum protein, such as alpha-1-microglobulin, AGP-1, albumin, vitamin D binding protein, hemopexin, afamin, or haptoglobin. When the fusion component is a molecule capable of binding a serum protein, it may be a small molecule, a nucleic acid, a peptide, or an oligosaccharide. It may also be a protein such as Fc gamma R1, ScFv, etc. In preferred embodiments, the fusion component is encoded by the nucleic acid, which encodes the fusion polypeptide of the invention. In some embodiments, however, such as when the fusion component is an oligosaccharide, the fusion component is attached post-translationally to the expressed fusion polypeptide.

The nucleic acid molecule of the invention may further optionally comprise a signal sequence (SS) component. When a SS is part of the polypeptide, any SS known to the art may be used, including synthetic or natural sequences from any source, for example, from a secreted or membrane bound protein. In one preferred embodiment, an ROR signal sequence is used (SEQ ID NO:6).

In a related second aspect, the invention features a vector comprising a nucleic acid molecule of the invention. In further third and fourth aspects, the invention encompasses vectors comprising the nucleic acid molecules of the invention, including expression vectors comprising the nucleic acid molecules operatively linked to an expression control sequence, and host-vector systems for the production of a fusion polypeptide which comprise the expression vector, in a suitable host cell; host-vector systems, wherein the suitable host cell is, without limitation, a bacterial, yeast, insect, mammalian cell or plants, such as tobacco, or animals such as cows, mice, or rabbits. Examples of suitable cells include *E. coli, B. subtilis*, BHK, COS and CHO cells. Additionally encompassed are fusion polypeptides of the invention modified by acetylation or pegylation.

In a related fifth aspect, the invention features a method of producing a fusion polypeptide of the invention, comprising culturing a host cell transfected with a vector comprising a nucleic acid molecule of the invention, under conditions suitable for expression of the protein from the host cell, and recovering the polypeptide so produced.

In sixth, seventh, and eighth aspects, the invention features an IL-4 and IL-13 fusion polypeptide comprising $(R1)_x$-$(R2)_y$-F, wherein R1, R2, F, x and y are as defined above. X and y are preferably each a number between 1-3; preferably, x and y are each 1.

In a ninth aspect, the invention features a multimeric polypeptide, comprising two or more fusion polypeptides of the invention. In more specific embodiment, the multimeric polypeptide is a dimer. The dimeric IL-4/13-specific fusion polypeptides of the invention are capable of inhibiting both IL-4 and IL-13 with an IC50 of at least $10^{-10}$ molar, as determined by assay methods known in the art. IC50 may, for example, be determined with the TF1 bioassay described below. Generally, the ability of the dimeric IL-4/13 fusion polypeptides to inhibit (e.g., block) the biological activity of hIL-4 and hIL-13, may be measured, for example, by bioassay or ELISA for free and/or bound ligand. Bioassays may include luciferase-based assays using an STAT6 promoter element, and/or hIL-4 or hIL-13 stimulation of cell lines such as TF1 or of human peripheral blood cells with readouts such as growth or sCD23 secretion. In different embodiments of the dimeric IL-4/13 polypeptides of the invention, the R1 component is modified to exhibit an increased or decreased ability to block hIL-4 activity and/or hIL-13 activity and/or the R2 component is modified to exhibit an increased or decreased ability to block IL-4 activity and/or IL-13 activity.

In a tenth aspect, the invention features pharmaceutical compositions comprising a fusion polypeptide of the invention with a pharmaceutically acceptable carrier. Such pharmaceutical compositions may comprise a monomeric or multimedc polypeptide, or nucleic acids encoding the fusion polypeptide.

The IL-4/13-specific polypeptides of the invention are therapeutically useful for treating any disease or condition, which is improved, ameliorated, or inhibited by removal, inhibition, or reduction of IL-4 and/or IL-13. These polypeptides are particularly useful for the treatment of conditions, such as asthma, which are improved, ameliorated, or inhibited by removal, inhibition, or reduction of IL-4 and IL-13. Accordingly, in a further aspect, the invention features a therapeutic method for the treatment of an IL-4 and/or IL-13-related disease or condition, comprising administering a fusion polypeptide of the invention to a subject suffering from an IL-4 and/or IL-13-related disease or condition. Although any mammal can be treated by the therapeutic methods of the invention, the subject is preferably a human patient suffering from or at risk of suffering from a condition or disease which can be improved, ameliorated, inhibited or treated with a fusion polypeptide of the invention.

In a further aspect, the invention further features diagnostic and prognostic methods, as well as kits for detecting, quantifying, and/or monitoring IL-4 and/or IL-13 with the fusion polypeptides of the invention.

Other objects and advantages will become apparent from a review of the ensuing detailed description.

DETAILED DESCRIPTION OF THE INVENTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to describe the methods and/or materials in connection with which the publications are cited.

Definitions

The term "affinity for" IL-4 and/or IL-13 means that the fusion polypeptide of the invention binds the intended cytokine(s) with an affinity of at least $10^{-10}$ molar, preferably at least $10^{-11}$ molar, as determined by assay methods known in the art, for example, BiaCore analysis. The term "capable of specifically blocking" or "capable of inhibiting the activity of" IL-4 and/or IL-13, means the IL-4/13 fusion polypeptides of the invention inhibit the biological activity of the target cytokines, as measured, for example, by bioassay or ELISA for free and/or bound ligand. Bioassays may include luciferase-based assays using an STAT6 promoter element, and/or IL-4 or IL-13 stimulation of cell lines such as TF1 or of human peripheral blood cells with readouts such as growth or sCD23 secretion. "IC50" is defined as the concentration of fusion protein required to inhibit 50% of the response to IL-4 or IL-13 as measured in a bioassay. The fusion polypeptides of the invention are preferably capable of inhibiting the biological activity of IL-4 and/or IL-13 with an IC50 of at least $1\times10^{-10}$ M (for both), even more preferably $10^{-11}$ M (for IL-13).

The terms "treatment", "treating", and the like are used herein to generally mean obtaining a desired pharmacologic and/or physiologic effect. The effect may be prophylactic in terms of completely or partially preventing a disease, condition, or symptoms thereof, and/or may be therapeutic in terms of a partial or complete cure for a disease or condition and/or adverse effect attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; or (c) relieving the disease or condition, i.e., causing regression of the disease or condition. The population of subjects treated by the method of the invention includes subjects suffering from the undesirable condition or disease, as well as subjects at risk for development of the condition or disease.

By the term "therapeutically effective dose" is meant a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

As used herein, a "condition or disease" generally encompasses a condition of a mammalian host, particularly a human host, which is undesirable and/or injurious to the host. Thus, treating a condition or disorder with a IL-4/13-specific fusion polypeptide will encompass the treatment of a mammal, in particular, a human, who has symptoms reflective of elevated or deleterious IL-4 and/or IL-13, or who is expected to have such decreased activation in response to a disease, condition or treatment regimen. Treating an IL-4 and/or IL-13-related condition or disease encompasses the treatment of a human subject wherein reducing IL-4 and/or IL-13 levels with the fusion polypeptide of the invention results in amelioration of an undesirable symptom resulting from the IL-4 and/or IL-13-related condition or disease.

General Description

Studies in animals lacking IL-4 and IL-13 have indicated that these cytokines play both overlapping and additive roles in the induction of Th2-like responses such as eosinophil infiltration, immunoglobulin E production and IL-5 production (McKenzie et al. (1999) J. Exp. Med. 189(10): 1565-72). The present invention provides novel polypeptides, both monomers and multimers, capable of acting as IL-4 and/or IL-13-specific fusion polypeptides or antagonists capable of binding IL-4 and/or IL-13 and blocking these biological actions.

Nucleic Acid Constructs and Expression

The present invention provides for the construction of nucleic acid molecules encoding IL-4/13 specific polypeptides. As described above, the nucleic acid molecules of the invention encode modified fragments of the wild-type (or naturally occurring) human IL-4Rα and/or IL-13Rα proteins. Accordingly, the nucleic acid molecules may be termed "recombinant", "artificial", or "synthetic" as they are not nucleic acid molecules found in nature, e.g., not naturally occurring sequences, but are sequences constructed by recombinant DNA technology.

These nucleic acid molecules are inserted into a vector that is able to express the fusion polypeptides of the invention when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion polypeptides of the invention under control of transcriptional and/or translational control signals.

Expression of the nucleic acid molecules of the invention may be regulated by a second nucleic acid sequence so that the molecule is expressed in a host transformed with the recombinant DNA molecule. For example, expression may be controlled by any promoter/enhancer element known in the art. Promoters which may be used to control expression of the chimeric polypeptide molecules include, but are not limited to, a long terminal repeat (Squinto et al. (1991) Cell 65:1-20); SV40 early promoter region, CMV, M-MuLV, thymidine kinase promoter, the regulatory sequences of the metallothionine gene; prokaryotic expression vectors such as the beta-lactamase promoter, or the tac promoter (see also Scientific American (1980) 242:74-94); promoter elements from yeast or other fungi such as Gal 4 promoter, ADH, PGK, alkaline phosphatase, and tissue-specific transcriptional control regions derived from genes such as elastase I.

Expression vectors capable of being replicated in a bacterial or eukaryotic host comprising the nucleic acid molecules of the invention are used to transfect the host and thereby direct expression of such nucleic acids to produce the fusion polypeptides of the invention. Transfected cells may transiently or, preferably, constitutively and permanently express the polypeptides of the invention. When the polypeptide so expressed comprises a fusion component such as a multimerizing component capable of associating with a multimerizing component of a second polypeptide, the monomers thus expressed multimerize due to the interactions between the multimerizing components to form a multimeric polypeptide (WO 00/18932, herein specifically incorporated by reference).

The fusion polypeptides of the invention may be purified by any technique known in the art. When the polypeptides of the invention comprise a multimerizing component, which spontaneously forms a multimer with another polypeptide, the purification techniques used allow for the subsequent formation of a stable, biologically active multimeric polypeptide, also known as a "fusion polypeptide". For example, and not by way of limitation, the factors may be recovered from cells either as soluble proteins or as inclusion bodies, from which they may be extracted quantitatively by 8M guanidinium hydrochloride and dialysis (see, for example, U.S. Pat. No. 5,663,304). In order to further purify the factors, conventional ion exchange chromatography, hydrophobic interaction chromatography, reverse phase chromatography or gel filtration may be used.

Fusion Components

The fusion polypeptides of the invention comprise a fusion component (F) which, in specific embodiments, is selected from the group consisting of a multimerizing component, a serum protein, or a molecule capable of binding a serum protein. When F is a multimerizing component, it includes any natural or synthetic sequence capable of interacting with another multimerizing component to form a higher order structure, e.g., a dimer, a trimer, etc. The multimerizing component may be selected from the group consisting of (i) a multimerizing component comprising a cleavable region (C-region), (ii) a truncated multimerizing component, (iii) an amino acid sequence between 1 to about 500 amino acids in length, (iv) a leucine zipper, (v) a helix loop motif, and (vi) a coil-coil motif. When F is a multimerizing component comprising an amino acid sequence between 1 to about 500 amino acids in length, the sequence may contain one or more cysteine residues capable of forming a disulfide bond with a corresponding cysteine residue on another fusion polypeptide comprising an F with one or more cysteine residues.

In a preferred embodiment, the multimerizing component comprises one or more immunoglobulin-derived domain from human IgG, IgM or IgA. In specific embodiments, the immunoglobulin-derived domain is selected from the group consisting of the Fc domain of IgG or the heavy chain of IgG. The Fc domain of IgG may be selected from the isotypes IgG1, IgG2, IgG3, and IgG4, as well as any allotype within each isotype group. In one specific embodiment, F is the Fc domain of IgG4 with Ser 228 (Cabot numbering) mutated to Pro to stabilize covalent dimer formation (Mol. Immunol. (1993) 30:105-108) and/or Leu235→Glu which eliminates residual effector functions (Reddy et al. (2000) J. Immunol. 164:1925-1933). In a preferred embodiment, F is the Fc domain of IgG1, or a derivative thereof which may be modified for specifically desired properties (see, for example, Armour et al. (2003) Mol. Immunol. 40:585-593; Shields et al. (2001) J. Biol. Chem. 276:6591-6604). In specific embodiments, the IL-4/13-specific polypeptide of the invention comprises one or two Fc domain(s) of IgG1.

In one embodiment, F is a serum protein or fragment thereof, is selected from the group consisting of α-1-microglobulin, AGP-1, orosomuciod, α-1-acid glycoprotein, vitamin D binding protein (DBP), hemopexin, human serum albumin (hSA), transferrin, ferritin, afamin, haptoglobin, α-fetoprotein thyroglobulin, α-2-HS-glycoprotein, β-2-glycoprotein, hyaluronan-binding protein, syntaxin, C1R, C1q a chain, galectin3-Mac2 binding protein, fibrinogen, polymeric Ig receptor (PIGR), α-2-macroglobulin, urea transport protein, haptoglobin, IGFBPs, macrophage scavenger receptors, fibronectin, giantin, Fc, α-1-antichyromotrypsin, α-1-antitrypsin, antithrombin III, apolipoprotein A-I, apolipoprotein B, β-2-microglobulin, ceruloplasmin, complement component C3 or C4, CI esterase inhibitor, C-reactive protein, cystatin C, and protein C. In a more specific embodiment, F is selected from the group consisting of α-1-microglobulin, AGP-1, orosomuciod, α-1-acid glycoprotein, vitamin D binding protein (DBP), hemopexin, human serum albumin (hSA), afamin, and haptoglobin. The inclusion of an F component may extend the serum half-life of the IL-4/13 specific polypeptide of the invention when desired. See, for example, U.S. Pat. Nos. 6,423,512, 5,876,969, 6,593,295, and 6,548,653, herein specifically incorporated by reference in their entirety, for examples of serum albumin fusion proteins. hSA is widely distributed throughout the body, particularly in the intestinal and blood components, and has an important role in the maintenance of osmolarity and plasma volume. It is slowly cleared in the liver, and typically has an in vivo half-life of 14-20 days in humans (Waldmann et al. (1977) *Albumin, Structure Function and Uses*; Pergamon Press; pp. 255-275).

When F is a molecule capable of binding a serum protein, the molecule may be a synthetic small molecule, a lipid or liposome, a nucleic acid, including a synthetic nucleic acid such as an aptomer, a peptide, or an oligosaccharide. The molecule may further be a protein, such as, for example, FcγR1, FcγR2, FcγR3, polymeric Ig receptor (PIGR), ScFv, and other antibody fragments specific for a serum protein.

Optional Component Spacers

The components of the fusion polypeptides of the invention may be connected directly to each other or be connected via spacers. Generally, the term "spacer" (or linker) means one or more molecules, e.g., nucleic acids or amino acids, or non-peptide moieties, such as polyethylene glycol, which may be inserted between one or more component domains. For example, spacer sequences may be used to provide a desirable site of interest between components for ease of manipulation. A spacer may also be provided to enhance expression of the fusion protein from a host cell, to decrease steric hindrance such that the component may assume its optimal tertiary structure and/or interact appropriately with its target molecule. For spacers and methods of identifying desirable spacers, see, for example, George et al. (2003) Protein Engineering 15:871-879, herein specifically incorporated by reference. A spacer sequence may include one or more amino acids naturally connected to a receptor component, or may be an added sequence used to enhance expression of the fusion protein, provide specifically desired sites of interest, allow component domains to form optimal tertiary structures and/or to enhance the interaction of a component with its target molecule. In one embodiment, the spacer comprises one or more peptide sequences between one or more components which is (are) between 1-100 amino acids, preferably 1-25. In one specific embodiment, the spacer is a three amino acid sequence; more specifically, the three amino acid sequence of Gly Ser Gly.

Inhibition of IL-4 and/or IL-13 Biological Activity

The fusion polypeptides of the invention are capable of inhibiting the biological activity of IL-4 and/or IL-13 with an IC50 (concentration of fusion protein required to inhibit 50% of the response to IL-4 or IL-13) of at least $1\times10^{-10}$ M; preferably $10^{-11}$ M (for IL-13). The data presented in Tables 1-7 below was determined in a TF1 bioassay for growth stimulated by IL-4 or IL-13, as described below. Other bioassays useful to determine IC50 are known to the art, including for example, luciferase-based assays using an STAT6 promoter element, and/or hIL-4 or hIL-13 stimulation of human peripheral blood cells with a readout such as sCD23 secretion. Data shown below in Tables 1-7 is shown as fold difference from parental molecule (IC50 value of the variant fusion polypeptide divided by the value of the IC50 of the parental 1132 molecule). As established in the experiments below, variant fusion polypeptides may have a 1.5 to 3.0-fold or even higher improved ability to block IL-4 and/or IL-13 relative to the parent molecule. In specific embodiments, the variant fusion polypeptide of the invention has at least a 2.0-fold improvement or greater, at least a 2.5-fold improvement or greater, or even at least a 3-fold improvement or greater in the ability to block IL-4 and/or IL-13.

Therapeutic Uses

The fusion polypeptides of the invention are therapeutically useful for treating any disease or condition which is improved, ameliorated, inhibited or prevented by removal, inhibition, or reduction of IL-4 and/or IL-13. IL-4 and IL-13 both independently, and jointly, have been implicated in a variety of clinical conditions, such as eosinophil infiltration, IgE production and IL-5 production, that are characterized by a Th2 cell-driven response. Accordingly, the blocking of these responses by the fusion polypeptide will be useful for the treatment of any disease or condition in which there is increased occurrence of T-helper cells of the TH2 type.

In one embodiment, the IL-4/13 fusion polypeptide is used to treat asthma. Data derived from animal experiments and examination of asthmatic humans implicate IL-4 and IL-13 as critical initiators of the atopic condition and perpetuators of the chronic inflammatory state that typifies the asthmatic lung. IL-4 and IL-13 induce effects that are associated with the asthmatic phenotype, including isotype switching to IgE production, eosinophilia, mastocytosis, mucus formation, increased vascular permeability, airway hyper-responsiveness, smooth muscle hyperplasia, and subepithelial fibrosis (Hogan et al. (1997) Pharmcol. Ther. 74(3):259-283; McKenzie et al. (2000) Pharmacol. Ther. 88(2):143-151; Wills-Karp (2001) J. Allergy Clin. Immunol. 107(1):9-18). Indeed, IL-4 and IL-13 signaling are required in mice for the development of an IgE response to an allergen, and development of an asthmatic response against ovalbumin is attenuated in IL-4Ra-deficient mice. Moreover, transgenic expression of IL-4 or IL-13 in the lungs of mice leads to an asthmatic phenotype, which can be mimicked by direct administration of IL-4 or IL-13 protein into the murine lung. Blocking of IL-4 and IL-13, therefore, is expected to lead to a mitigation in some or all of the above-mentioned parameters. Furthermore, because of the ability of either IL-4 or IL-13 to independently initiate the signaling cascade and induce the asthma phenotype, inhibiting both molecules at the same time may lead to more potent anti-asthma effectiveness.

A non-exhaustive list of specific conditions improved by inhibition or reduction of IL-4 and/or IL-13 include atopic dermatitis, immune complex disease (such as lupus, nephritis, and Grave's disease) allergic conditions, hyper IgE syndrome, immune deficiencies, idiopathic pulmonary fibrosis, hepatic fibrosis, HIV, pulmonary 'remodeling', COPD, ulcerative colitis, cancer, Hodgkin's Lymphoma, bullous pemphigoid, transplant and graft vs host disease viral, parasitic, bacterial disease and fungal infection. (U.S. Pat. No. 6,328,954 issued Dec. 11, 2001. ldzerda, R. J. et al. 1990 J Exp. Med. 171:861-873.

In alternative embodiments, the fusion polypeptide is used as an adjuvant with a vaccine to push the immune response to one of cell-mediated immunity, which is often accompanied by changes in Ig isotypes as well as a CTL (cytotoxic T lymphocyte) response. CTLs are primarily CD8 positive T cells, which aid in the destruction of virally or intracellular bacteria infected cells and tumor cells.

Suitable Subject for Treatment

A suitable subject for treatment is a human diagnosed as suffering from specific conditions improved by inhibition or reduction of IL-4 and/or IL-13 include atopic dermatitis, immune complex disease (such as lupus, nephritis, and Grave's disease) allergic conditions, hyper IgE syndrome, immune deficiencies, idiopathic pulmonary fibrosis, hepatic fibrosis, HIV, pulmonary 'remodeling', COPD, ulcerative colitis, cancer, Hodgkin's Lymphoma, bullous pemphigoid, transplant and graft vs host disease viral, parasitic, bacterial disease and fungal infection.

Combination Therapies

In numerous embodiments, the fusion polypeptides of the invention may be administered in combination with one or more additional compounds or therapies. Combinations include, short-acting inhaled beta2 agonists, oral beta2 agonists, inhaled anticholinergics, oral corticosteroids, inhaled corticosteroids, cromolyn sodium (Gastrocrom/Celltech), nedocromil, long-acting beta2 agonists, leukotriene modifiers, theophylline, calcinerin inhibitors, picrolimus, sirolimus, anti-IgE (Zolair. Genentech), NFKB inhibitors, p38 MAP kinase inhibitors (VX-702), ICE inhibitors (VX-765), IL-1 inhibitors (IL-1-specific fusion polypeptide, Regeneron; anakinra, Amgen), TNFa inhibitors (Remicade, Centocor; Enbrel, Amgen; Humira, Abbott), IL-5 inhibitors, IL-18 inhibitors, IFNgamma inhibitors, IFNalpha blockers. For example, multiple fusion polypeptides can be co-administered, or one or polypeptide can be administered in conjunction with one or more therapeutic compounds. When a polypeptide of the invention removes IL-4 and/or IL-13, the one or more other therapeutic agent is one that is used to prevent or treat a condition associated with the presence of IL-4 and/or IL-13. A benefit of the combined use of the fusion polypeptide of the invention with a second therapeutic agent is that it provides improved efficacy and/or reduced toxicity of either therapeutic agent.

Methods of Administration

The invention provides methods of treatment comprising administering to a subject an effective amount of a fusion polypeptide of the invention. In a preferred aspect, the fusion polypeptide is substantially purified (e.g., substantially free from substances that limit its effect or produce undesired side-effects). The subject is preferably a mammal, and most preferably a human.

Various delivery systems are known and can be used to administer an agent of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intra-articular, infusion polypeptideeritoneal, intravenous, subcutaneous, intranasal, intraocular, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration can be acute or chronic (e.g. daily, weekly, monthly, etc.) or in combination with other agents. Pulmonary administration can also be employed, e.g., by use of an inhaler or nebulizer, and formulation with an aerosolizing agent.

In another embodiment, the active agent can be delivered in a vesicle, in particular a liposome, in a controlled release system, or in a pump. In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), by direct injection, or by use of microparticle bombardment, or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination. Systemic expression may also be achieved by plasmid injection (intradermally or intramuscularly) and electroporation into cells.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

A composition useful in practicing the methods of the invention may be a liquid comprising an agent of the invention in solution, in suspension, or both. The term “solution/suspension” refers to a liquid composition where a first portion of the active agent is present in solution and a second portion of the active agent is present in particulate form, in suspension in a liquid matrix. A liquid composition also includes a gel. The liquid composition may be aqueous or in the form of an ointment.

In one embodiment, the pharmaceutical composition of the invention is a sustained release composition. Sustained release formulations for delivery of biologically active peptides are known to the art. For example, U.S. Pat. No. 6,740,634, herein specifically incorporated by reference in its entirety, describes a sustained-release formulation containing a hydroxynaphtoic acid salt of a biologically active substance and a biodegradable polymer. U.S. Pat. No. 6,699,500, herein specifically incorporated by reference in its entirety, discloses a sustained-release formulation capable of releasing a physiologically active substance over a period of at least 5 months.

Diagnostic and Screening Methods

The fusion polypeptides of the invention may be used diagnostically and/or in screening methods. For example, the fusion polypeptide may be used to monitor levels of IL-4 and/or IL-13 during a clinical study to evaluate treatment efficacy. In another embodiment, the methods and compositions of the present invention are used to screen individuals for entry into a clinical study to identify individuals having, for example, too high or too low a level of IL-4 and/or IL-13. The fusion polypeptides of the invention can be used in methods known in the art relating to the localization and activity of IL-4 and/or IL-13, e.g., imaging, measuring levels thereof in appropriate physiological samples, in diagnostic methods, etc.

The fusion polypeptides of the invention may be used in in vivo and in vitro screening assay to quantify the amount of non-bound IL-4 and/or IL-13 present, e.g., for example, in a screening method to identify test agents able to decrease the. expression of IL-4and/or IL-13. More generally, the fusion polypeptides of the invention may be used in any assay or process in which quantification and/or isolation of IL-4 and/or IL-13 is desired.

Pharmaceutical Compositions

The present invention also provides pharmaceutical compositions comprising a fusion polypeptide of the invention. Such compositions comprise a therapeutically effective amount of one or more fusion polypeptide(s), and a pharmaceutically acceptable carrier. The term “pharmaceutically acceptable” means approved by a regulatory agency of the Federal or a state government or listed in the U.S. Pharmacopeia or other generally recognized pharmacopeia for use in animals, and more particularly, in humans. The term “carrier” refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in “Remington's Pharmaceutical Sciences” by E. W. Martin.

The fusion polypeptide of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the fusion polypeptide that will be effective for its intended therapeutic use can be determined by standard clinical techniques based on the present description. In addition, in vitro assays may optionally be employed to help identify optimal dosage ranges. Generally, suitable dosage ranges for intravenous administration are generally about 0.02-10 milligrams active compound per kilogram body weight. Suitable dosage ranges for intranasal administration are generally about 0.01 pg/kg body weight to 10 mg/kg body weight. Effective doses may be extrapolated from dose-response curves derived from in vitro or animal model test systems. The amount of compound administered will, of course, be dependent on the subject being treated, on the subject's weight, the severity of the affliction, the manner of administration, and the judgment of the prescribing physician. The therapy may be repeated intermittently while symptoms are detectable or even when they are not detectable.

Cellular Transfection and Gene Therapy

The present invention encompasses the use of nucleic acids encoding the fusion polypeptides of the invention for transfection of cells in vitro and in vivo. These nucleic acids can be inserted into any of a number of well-known vectors for transfection of target cells and organisms. The nucleic acids are transfected into cells ex vivo and in vivo, through the interaction of the vector and the target cell facilitated by lipid mixes or electroporation. The compositions are administered (e.g., by injection into a muscle) to a subject in an amount sufficient to elicit a therapeutic response. An amount adequate to accomplish this is defined as "a therapeutically effective dose or amount."

In another aspect, the invention provides a method of reducing IL-4 and/or IL-13 levels in a human or other animal comprising transfecting a cell with a nucleic acid encoding a polypeptide of the invention, wherein the nucleic acid comprises an inducible promoter operably linked to the nucleic acid encoding the polypeptide. For gene therapy procedures in the treatment or prevention of human disease, see for example, Van Brunt (1998) Biotechnology 6:1149-1154.

Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Construction of IL-4/13 Variant Fusion Polypeptides

To create the parental IL-4/13 fusion polypeptide, 1132 (SEQ ID NO:8), nucleic acids encoding the human IL-4Rα extracellular domain (SEQ ID NO:1-2) and the human IL-13Rα1 extracellular domain (27-343 of SEQ ID NO:3) were amplified using standard PCR techniques, and were ligated into an expression vector which contained the human Fc sequence, thus creating fusion protein consisting of the IL-4Rα and/or IL-13Rα1, and the hinge, CH2 and CH3 regions of human IgG1 from the N to C terminus. Substitutions Cys207→Ser of SEQ ID NO:8 and Cys251→Ala of SEQ ID NO:8 (Cys251 corresponds to Cys46 of SEQ ID NO:3) were introduced by site-directed mutagenesis using standard techniques know to the art. All sequences were verified by standard techniques. The appropriate coding sequence was subcloned into an eukaryotic expression vector using standard molecular biology techniques. IL-4/13 fusion polypeptide variants were created by site-directed mutagenesis of the parent 1132 fusion polypeptide using techniques known to the art, and confirmed by sequencing.

Variant IL-4/13 fusion polypeptides were produce as small-scale supernatants by transiently transfecting CHO cells, using Lipofectamine/LIPO Plus™ (Life Technologies), with DNA constructs encoding variant proteins. Supernatants were collected after 72 hours and protein expression was measured by Western blotting with anti-human Fc HRP-conjugated antibody (Promega) and visualized by ECL (Pierce). For large-scale purification of the variant IL/4/13 fusion polypeptides, DNA encoding the fusion protein was transfected into CHO cells for either transient expression or to create stable lines using FASTR technology (US patent application publication 20020168702). Culture medium from 1-2 liters of the cells that express the fusion protein was collected and passed through a Protein A column to capture the Fc containing fusion protein. The protein A purification was performed according to the manufacturer's protocol (Amersham). After concentration, the fusion protein was characterized for the percentage of contaminating aggregates and further purified using Size Exclusion Chromatography (SEC) using a Superdex 200 column (Amersham) or similar column.

The stability of the variant IL-4/13 fusion polypeptides was assessed using standard methods, including analysis by SEC and western blot after 20 freeze/thaw cycles, incubating the protein at 37° C. for 7 days in low (10 mM Sodium Phosphate buffer) and medium salt (PBS) buffers, or incubating the protein in a PBS solution buffered at a variety of pHs for two hours.

Pharmacokinetics of the molecules was determined by injecting mice or rats with 1 mg/kg of the IL-4/13 fusion polypeptide variant intravenously or subcutaneously, blood was collected at various time points, and serum was isolated. Serum samples were analyzed for the quantity of variant fusion polypeptides using an ELISA with an anti-IL-13Ra monoclonal antibody to capture the fusion protein, a biotinylated anti-IL-4Ra monoclonal antibody to form a complex, and a Streptavidin-HRP conjugate to detect the complex. Fusion polypeptide concentrations were determined by comparison of the OD from the serum samples to the ODs obtained from a standard curve produced using the purified fusion protein. Fusion polypeptide quality was also monitored by Western blot analysis of 1 ul of serum using one of three antibodies, anti-IL-13Ra, anti-IL-4Ra or anti-human Fc antibodies and an HRP-conjugated secondary antibody for detection.

Example 2

Inhibition of hIL-4 and hIL-13 Bloactivity by Variant Fusion Polypeptides

TF1 Bioassay. TF1 cells that had been stably transfected with hIL-13Rα1 were maintained in growth media (10 ng/ml GM-CSF, RPMI 1640, 10% FBS, L-glutamine, Penicillin, Streptomycin). For the bioassay, cells are washed 3 times in assay media (as above but without GM-CSF) and then plated at $2\times10^4$ cells in 50 μl of assay media. The purified fusion polypeptides were serially diluted into assay media. 25 ul of each of the variant IL-4/13 fusion polypeptides was added to the cells. 25 μl of either IL-13 (15 pM) or IL-4 (20 or 40 pM) was then added to the wells containing the cells and the fusion polypeptides. Cells were then incubated at 37° C., 5% $CO_2$ for ~70 hrs. The extent of TF1 cell proliferation was measured by the CCK-8 assay according to the manufacturer's protocol (Dojindo Laboratories).

All bioassays for Tables 1-7 included the parental IL-4/13 fusion polypeptide, 1132 (SEQ ID NO:8 shown with a signal sequence which is removed from the mature polypeptide) (encoded by SEQ ID NO:7), which consists of a signal sequence (amino acids 1-23)+an IL-4Rα component (amino acids 24-231 of SEQ ID NO:8 with Cys207→Ser) (corresponding to 24-231 of SEQ ID NO:2)+an IL-13Rα1 component (amino acids 232-548 of SEQ ID NO:8 with Cys251→Ala) (Cys251 corresponds to Cys46 of SEQ ID NO:3) (corresponding to 27-343 of SEQ ID NO:3)+a multimerizing component (IgG1 Fc) (549-776 of SEQ ID NO:8). All variant fusion polypeptides, except those specified otherwise (Table 1) contain the parent Cys207→Ser mutation, and all variant fusion polypeptides contain the Cys251→Ala (Cys 46 of SEQ ID NO:3) mutation in the IL-13Ra1 component. See for example, SEQ ID NO:10 (construct 2674; encoded by SEQ ID NO:9), SEQ ID NO:12 (construct 2681; encoded by SEQ ID NO:11), SEQ ID NO:14 (construct 2795; encoded by SEQ ID NO:13), and SEQ ID NO:16 (construct 2796; encoded by SEQ ID NO:15) which include a signal sequence ultimately cleaved from the mature fusion polypeptide). Table 1 shows IC50 data (the concentration at which 50% of the cell growth is inhibited) for the parental trap, 1132, and two example variant fusion proteins, as well as the fold difference from the IC50 value for the parental IL-4/13 fusion polypeptide 1132 (parent fusion polypeptide IC50 divided by variant fusion polypeptide IC50).

TABLE 1

IC50 and Fold Difference Data for Fusion Polypeptides 2674 and 2681

| Construct | IL-4 IC50 (pM) | IL-13 IC50 (pM) | IL-4 Fold Difference | IL-13 Fold Difference |
|---|---|---|---|---|
| 1132 | 141 ± 49 | 21 ± 9 | | |
| 2674 | 64 ± 30 | 10 ± 5 | 2.3 ± 0.7 | 2.3 ± 0.6 |
| 2681 | 41 ± 14 | 9 ± 4 | 3.65 ± 1.4 | 2.5 ± 0.8 |

Tables 2 through 6 show fold difference of IC50 bioassay values of the variant fusion polypeptides assayed using CHO transient supernatants, whose concentrations were determined by Western blot analysis. Table 2 shows the fold difference in IC50s for ability of variants having cysteine mutations to block hIL-13 or hIL-4 activity; Table 3 shows the ability of fusion polypeptide variants having core stabilizing and active site mutations to block hIL-13 or hIL-4 activity; Table 4 shows charge change variants and combinations to block hIL-13 or hIL-4 activity; Table 5 shows hydrophobic patch variants and combinations to block hIL-13 or hIL-4 activity; Table 6 shows the activity of variant fusion polypeptides with IL-4Rα N and C terminal deletions (all expressed relative to parent fusion polypeptide 1132).

TABLE 2

Ability of Cysteine Variants To Block IL-13 and IL-4 Activity

| Construct # | Changes from Parent Molecule | IL-13 Inhibition | IL-4 Inhibition |
|---|---|---|---|
| 405 | C207S, 13Rα1C46A (parent molecule) | 1 | 1 |
| 2576 | C207, 13Rα1C46A | 0.09-0.15 | 0.71-1.22 |
| 2594 | C207, 13Rα1C46 | 0.01 | 0.22 |
| 2615 | C207S, 13Rα1C46 | 0.58-1.29 | 0.65-1.04 |
| 2575 | Q206H, C207, 13Rα1C46 | 0.01 | 0.35 |
| 2551 | C207H | 0.07-0.13 | 0.50-0.84 |
| 2588 | C207N | 0.23-0.40 | 0.92-1.38 |
| 2589 | C207D | 0.9-0.15 | 0.57-0.61 |
| 2590 | C207E | 0.06-0.10 | 0.63-0.68 |
| 2591 | C207Y | 0.03-0.04 | 1.02-1.24 |
| 2642 | C207G | 0.24-0.27 | 1.18-1.53 |
| 2648 | C207A | 0.39-0.77 | 1.89-2.64 |
| 2684 | C207T | 0.07-0.67 | 0.30-0.41 |
| 2683 | C207A, L67Y, L68N, Y152F | 1.03 | 2.06 |
| 2682 | C207A, L67Y, L68N, D171Y, F172S | 0.95-2.25 | 1.48-4.81 |

TABLE 3

Ability of Core Stabilizing and Active Site Variants to Block IL-13 and IL-4 Activity

| Construct # | Changes from Parent 1132 | IL-13 Inhibition | IL-4 Inhibition |
|---|---|---|---|
| 2595 | S42I | 0.15 | 0.15 |
| 2596 | A105I | 0.44 | 1.12 |
| 2597 | A199I | 0.27 | 0.27 |
| 2598 | A203I | 0.10 | 0.22 |
| 2599 | A205I | 0.16 | 0.33 |
| 2600 | A203I, A205I | 0.06 | 0.68 |
| 2675 | L60K | 0.46 | (n/a) |
| 2676 | L60Q | 0.23 | (n/a) |
| 2677 | L60Y | 0.43 | (n/a) |
| 2707 | L64K | 0.03-0.04 | 0.04 |
| 2708 | L64Y | 0.03-0.06 | 0.04 |
| 2560 | Y152F | 0.73-0.98 | 0.97-1.71 |
| 2561 | Y152K | 0.15 | 0.16 |
| 2562 | Y152R | 0.19-0.40 | 0.07-0.16 |
| 2592 | D150N | 1.11-1.33 | 0.12-0.19 |
| 2593 | Y152H | 0.31-0.37 | 0.09-0.15 |
| 2601 | L67Q, L68S, Y152F | 0.77 | 0.31 |
| 2586 | Y152F, D171Y, F172S, Y175H | 0.53-0.80 | 1.06-1.08 |
| 2587 | Y152F, D171Y, F172S, Y175H, R198S | 0.50-0.57 | 0.70-1.02 |
| 2651 | L67Y, L68N, Y152F | 1.57-1.58 | 2.30-2.96 |

TABLE 4

Charge Variants and Combination Variants to Inhibit IL-4 and IL-13 Activity

| Construct | Modifications from Parent 1132 | IL-13 Inhibition | IL-4 Inhibition |
|---|---|---|---|
| 2549 | D171Y, F172S, Y175H | 0.32-1.91 | 0.28-1.97 |
| 2550 | R198S | 0.95-1.08 | 0.82-1.25 |
| 2558 | R198S, D171Y, F172S, Y175H | 0.39-1.02 | 0.39-0.94 |
| 2586 | Y152F, D171Y, F172S, Y175H | 0.53-0.80 | 1.06-1.08 |
| 2587 | Y152F, D171Y, F172S, Y175H, R198S | 0.50-0.57 | 0.70-1.02 |
| 2643 | E70G | 0.27 | <0.10 |
| 2644 | E119T | 0.21 | 0.36 |
| 2645 | E181A | 0.46-0.90 | 0.29-0.91 |
| 2646 | STLK189-192HDAW | 0.05 | <0.10 |
| 2647 | D171Y, F172S | 1.16-1.44 | 1.79-2.00 |
| 2653 | E181A, D171Y, F172S | 0.55-1.44 | 0.71-1.71 |
| 2680 | D171Y, F172S, Y152F | 0.72-1.00 | 1.01-1.30 |
| 2688 | D171Y | 1.46-1.93 | 1.46-1.68 |
| 2689 | F172S | 1.23-2.00 | 0.62-2.23 |
| 2699 | L67Y, D171Y | 0.81-1.77 | 0.84-1.59 |
| 2700 | L67Y, F172S | 1.22-1.56 | 0.91-0.98 |
| 2701 | L67Y, D171Y, F172S | 1.02-1.65 | 1.14-1.44 |
| 2702 | L68N, D171Y | 1.28-1.95 | 1.32-1.96 |
| 2703 | L68N, F172S | 0.79-1.79 | 0.55-0.98 |
| 2704 | L68N, D171Y, F172S | 1.10-2.29 | 1.01-2.07 |
| 2705 | L67Y, L68N, D171Y | 0.89-2.15 | 1.25-2.74 |
| 2706 | L67Y, L68N, F172S | 1.10-3.22 | 1.01-2.96 |

TABLE 5

Ability of Hydrophobic Patch and Combination Variants to Inhibit IL-13 and IL-4 Activity

| Construct | Changes From Parent 1132 | IL-13 Inhibition | IL-4 Inhibition |
|---|---|---|---|
| 2547 | L67Q, L68S | 0.45-0.90 | 0.13-0.24 |
| 2601 | L67Q, L68S, Y152F | 0.77 | 0.31 |
| 2602 | L67Y, L68N | 1.00-2.00 | 0.98-2.21 |
| 2649 | L67Y, L68N, D171Y, F172S, Y175H | 1.38-1.48 | 0.84-0.98 |
| 2650 | L67Y, L68N, R198S | 2.25-4.20 | 1.43-1.62 |
| 2651 | L67Y, L68N, Y152F | 1.57-1.58 | 2.30-2.96 |

TABLE 5-continued

Ability of Hydrophobic Patch and Combination Variants to Inhibit IL-13 and IL-4 Activity

| Construct | Changes From Parent 1132 | IL-13 Inhibition | IL-4 Inhibition |
|---|---|---|---|
| 2674 | L67Y, L68N, D171Y, F172S | 3.00-3.60 | 3.35-3.58 |
| 2681 | L67Y, L68N, D171Y, F172S, Y152F | 1.46-3.60 | 2.09-5.70 |
| 2686 | L67Y | 1.80-2.42 | 0.96-1.04 |
| 2687 | L68N | 1.44-1.62 | 0.82-0.87 |
| 2699 | L67Y, D171Y | 0.81-1.77 | 0.84-1.59 |
| 2700 | L67Y, F172S | 1.22-1.56 | 0.91-0.98 |
| 2701 | L67Y, D171Y, F172S | 1.02-1.65 | 1.14-1.44 |
| 2702 | L68N, D171Y | 1.28-1.95 | 1.32-1.96 |
| 2703 | L68N, F172S | 0.79-1.79 | 0.55-0.98 |
| 2704 | L68N, D171Y, F172S | 1.10-2.29 | 1.01-2.07 |
| 2705 | L67Y, L68N, D171Y | 0.89-2.15 | 1.25-2.74 |
| 2706 | L67Y, L68N, F172S | 1.10-3.22 | 1.01-2.96 |
| 2795 | L67Y, L68N, D171F, F172S | 3.5-4.3 | 3.3-4.9 |
| 2796 | L67Y, L68N, Y152F, D171F, F172S | 1.8-4.5 | 2.1-9.1 |
| 2797 | L67Y, L68N, D171A, F172S | 0.9-2.8 | 0.87-2.8 |
| 2798 | L67Y, L68N, Y152F, D171A, F172S | 1.4-3.1 | 1.7-4.8 |

TABLE 6

Ability of N- and C-Terminal Variants to Inhibit IL-13 and IL-4 Activity

| Construct # | Changes from Parent 1132 | IL-13 Inhibition | IL-4 Inhibition |
|---|---|---|---|
| 2713 | Deletion of aa 24-27 | 0.39-0.43 | 1.36-1.90 |
| 2714 | Deletion of aa 222-231 | 0.70-0.71 | 0.49-0.87 |

Example 3

Characterization of Purified Fusion Polypeptide Variants for Bioactivity

Table 7 shows the ability of purified variant fusion polypeptides to block IL-4 and IL-13 activity. The results are shown as the fold difference from the IC50 value for parental fusion polypeptide (the parent fusion polypeptide IC50 divided by variant fusion polypeptide IC50) IL-4/13 fusion polypeptide 1132 (SEQ ID NO:8). The parent molecule consists of a signal sequence (amino acids 1-23)+an IL-4Rα component (amino acids 24-231 with Cys207Ser) (corresponding to 24-231 of SEQ ID NO:2)+an IL-13Rα1 component (amino acids 232-548 with Cys251Ala) (corresponding to 27-343 of SEQ ID NO:3)+a multimerizing component (IgG1 Fc) (549-776). Standard errors are given for those that were assayed three or more times. All variant fusion polypeptides, except those with other specified substitutions of Cys207, contain the Cys207→Ser mutation, and all variant fusion polypeptides contain the Cys251→Ala mutation in the IL-13Rα1 component.

TABLE 7

Ability of Variant Molecules to Inhibit IL-13 and IL-4 Activity

| Construct | Changes from Parent Molecule 1132 | IL-13 Inhibition | IL-4 Inhibition |
|---|---|---|---|
| 2547 | L67Q, L68S | 1.49 | 0.24 |
| 2549 | D171Y, F172S, Y175H | 0.61 | 0.64 |
| 2558 | D171Y, F172S, Y175H, R198S | 0.43 | 0.63 |
| 2560 | Y152F | 1.4 ± 0.4 | 1.7 ± 0.3 |
| 2576 | S207C | 0.07 | 0.85 |
| 2586 | Y152F, D171Y, F172S, Y175H | 0.61 | 0.88 |
| 2594 | S207C, A228C | 0.02 | 0.55 |
| 2602 | L67Y, L68N | 2.2 ± 0.1 | 1.3 ± 0.1 |
| 2647 | D171Y, F172S | 1.6 ± 0.2 | 1.5 ± 0.1 |
| 2651 | L67Y, L68N, Y152F | 1.8 ± 0.2 | 2.0 ± 0.2 |
| 2674 | L67Y, L68N, D171Y, F172S | 2.3 ± 0.2 | 1.9 ± 0.1 |
| 2681 | L67Y, L68N, Y152F, D171Y, F172S | 2.2 ± 0.1 | 2.9 ± 0.2 |

Example 4

Determination of IL-4/13 Binding Affinity of Variants Using BIAcore

The affinity of the IL-4/13-specific polypeptides for human IL-4 and IL-13 was measured using a BIAcore 2000 or BIAcore 3000, as described in WO 00/75319, herein specifically incorporated by reference in its entirety. The BIAcore assay tested the parental 1132 (SEQ ID NO:8) construct relative to R1-R2-Fc variants, all of which consisted of a signal sequence, an IL-4Rα component, followed by an IL-13Rα1 component and a multimerizing component (IgG1 Fc). IL-4/13 fusion polypeptide variants were captured onto the chip surface using anti-human Fc antibodies. Various concentrations of human IL-4 and/or IL-13 were injected over the surface and the time course of association and dissociation was monitored. Kinetic analysis using BIA evaluation software was performed to obtain the association and dissociation rate constants. Results are shown in Table 8.

TABLE 8

IL-4/IL-13 Binding Affinity Measured via BIAcore

| Variant | IL-4 | | | IL-13 | | |
|---|---|---|---|---|---|---|
| | $K_D$ | $K_{ON}$ | $K_{OFF}$ | $K_D$ | $K_{ON}$ | $K_{OFF}$ |
| 1132 Parent | $1.04 \times 10^{-11}$ | $8.75 \times 10^{7}$ | $9.09 \times 10^{-4}$ | $4.56 \times 10^{-12}$<br>$4.11 \times 10^{-12}$ | $2.36 \times 10^{6}$<br>$3.11 \times 10^{6}$ | $1.08 \times 10^{-5}$<br>$1.28 \times 10^{-5}$ |
| 2547 L67Q, L68S | $4.79 \times 10^{-11}$ | $7.12 \times 10^{7}$ | $3.41 \times 10^{-3}$ | $2.73 \times 10^{-12}$ | $3.01 \times 10^{6}$ | $3.41 \times 10^{-3}$ |
| 2549 D171Y, F172S, Y175H | $1.09 \times 10^{-11}$ | $7.46 \times 10^{7}$ | $8.13 \times 10^{-4}$ | $1.09 \times 10^{-11}$ | $7.46 \times 10^{7}$ | $8.23 \times 10^{-6}$ |
| 2558 D171Y, F172S, Y175H, R198S | $3.18 \times 10^{-11}$ | $2.5 \times 10^{7}$ | $7.96 \times 10^{-4}$ | $1.63 \times 10^{-12}$ | $3.39 \times 10^{6}$ | $5.52 \times 10^{-6}$ |
| 2560 Y152F | $6.62 \times 10^{-12}$ | $8.8 \times 10^{7}$ | $5.87 \times 10^{-4}$ | $2.09 \times 10^{-12}$ | $2.21 \times 10^{6}$ | $4.61 \times 10^{-6}$ |
| 2576 S207C | $3.13 \times 10^{-11}$ | $5.37 \times 10^{7}$ | $1.66 \times 10^{-3}$ | $3.15 \times 10^{-12}$ | $4.02 \times 10^{6}$ | $1.26 \times 10^{-5}$ |

TABLE 8-continued

| | IL-4/IL-13 Binding Affinity Measured via BIAcore | | | | | |
|---|---|---|---|---|---|---|
| | IL-4 | | | IL-13 | | |
| Variant | $K_D$ | $K_{ON}$ | $K_{OFF}$ | $K_D$ | $K_{ON}$ | $K_{OFF}$ |
| 2586 Y152F, D171Y, F172S, Y175H | $2.07 \times 10^{-11}$ | $1.06 \times 10^{8}$ | $2.18 \times 10^{-3}$ | $2.17 \times 10^{-12}$ | $6.12 \times 10^{6}$ | $1.33 \times 10^{-5}$ |
| 2594 A228C | $3.45 \times 10^{-11}$ | $7.92 \times 10^{7}$ | $2.73 \times 10^{-3}$ | $9.71 \times 10^{-12}$ | $5.28 \times 10^{6}$ | $5.13 \times 10^{-5}$ |
| 2602 L67Y, L68N | $1.45 \times 10^{-11}$ | $6.90 \times 10^{7}$ | $1.00 \times 10^{-3}$ | $3.01 \times 10^{-12}$ | $1.12 \times 10^{7}$ | $3.36 \times 10^{-5}$ |
| 2647 D171Y F172S | $6.87 \times 10^{-12}$ | $4.80 \times 10^{7}$ | $3.30 \times 10^{-4}$ | $5.09 \times 10^{-12}$ | $1.07 \times 10^{7}$ | $5.44 \times 10^{-5}$ |
| 2651 L67Y, L68N, Y152F | $1.08 \times 10^{-11}$ | $5.15 \times 10^{7}$ | $5.57 \times 10^{-4}$ | $4.26 \times 10^{-12}$ | $7.83 \times 10^{6}$ | $3.34 \times 10^{-5}$ |
| 2674 L67Y, L68N, D171Y, F172S | $1.78 \times 10^{-11}$ | $1.94 \times 10^{8}$ | $3.46 \times 10^{-3}$ | $5.99 \times 10^{-12}$ | $3.33 \times 10^{6}$ | $2.00 \times 10^{-5}$ |
| 2681 L67Y, L68N, Y152F, D171Y, F172S | $9.54 \times 10^{-12}$ | $6.32 \times 10^{7}$ | $6.03 \times 10^{-4}$ | $4.96 \times 10^{-12}$ | $3.18 \times 10^{6}$ | $1.58 \times 10^{-5}$ |

Example 5

Ability of Component Variants to Inhibit IL-4 and IL-13 Activity

Table 9 shows fold differences of IC50 bioassay values of fusion polypeptides assayed using CHO transient supernatants as described above, These fusion polypeptides contain alternate component arrangements, e.g., R2-R1-F (SEQ ID NOs: 3 and 2) and are compared to the 1132 parental molecule. The tested variants are composed of ROR signal sequence (amino acids 1-29)+IL-13Rα1 component (amino acids 30-346 with Cys46Ser corresponding to 27-343 of SEQ ID NO:3)+an IL-4Rα component (amino acids 347-554 with Cys207Ser corresponding to 24-231 of SEQ ID NO:2)+a multimerizing component. (IgG1 Fc, amino acids 555-784).

TABLE 9

| Component Arrangement Variants | | | |
|---|---|---|---|
| Construct # | Changes from Parent 1132 | IL-13 Inhibition | IL-4 Inhibition |
| 2819 | R2-R1-Fc | 1.2-1.6 | 0.9-1.1 |
| 2821 | R2-R1(L67Y, L68N, Y152F, D171Y, F172S)-Fc | 2.0-2.4 | 3.2-3.9 |

We claim:

1. A nucleic acid molecule encoding fusion polypeptide $(R1)_x$-$(R2)_y$-F, wherein R1 is an interleukin-4 receptor α (IL-4Rα) component comprising a first amino acid sequence of amino acid residues 1-231 of SEQ ID NO:2, wherein one or more amino acids at positions 67, 68, 71, 152. 164, 171, 172, 175 and 198 are modified;

R2 is an interleukin-13 receptor α1 (IL-13Rα1) component comprising a second amino acid sequence of amino acid residues 27-343 of SEQ ID NO:3, wherein said second amino acid sequence may comprise one to three modifications;

F is a multimerizing component; and x and y are each independently a positive integer $\geqq 1$.

2. The nucleic acid molecule of claim 1, wherein the first amino acid sequence further comprises a modification at position 207.

3. The nucleic acid molecule of claim 1 or 2, wherein the amino acid at position 67 of the first amino acid sequence is substituted with Tyr.

4. The nucleic acid molecule of claim 1 or 2, wherein the amino acid at position 68 of the first amino acid sequence is substituted with Asn.

5. The nucleic acid molecule of claim 1 or 2, wherein the amino acid at position 171 of the first amino acid sequence is substituted with Tyr or Phe.

6. The nucleic acid molecule of claim 1 or 2, wherein the amino acid at position 172 of the first amino acid sequence is substituted with Ser.

7. The nucleic acid molecule of claim 1 or 2, wherein the amino acid at position 152 of the first amino acid sequence is substituted with Phe.

8. The nucleic acid molecule of claim 1 or 2, wherein the amino acid at position 198 of the first amino acid sequence is substituted with Ser.

9. The nucleic acid molecule of claim 2, wherein the amino acid at position 207 of the first amino acid sequence is substituted with Ser.

10. The nucleic acid molecule of claim 2, wherein the first amino acid sequence comprises substitutions at positions 67, 68 and 207.

11. The nucleic acid molecule of claim 10, wherein the amino acid at position 67 is substituted with Tyr.

12. The nucleic acid molecule of claim 10, wherein the amino acid at position 68 is substituted with Asn.

13. The nucleic acid molecule of claim 11, wherein the amino acid at position 68 is substituted with Asn.

14. The nucleic acid molecule of claim 10, wherein the first amino acid sequence is further substituted at positions 171 and 172.

15. The nucleic acid molecule of claim 14, wherein the amino acid at position 171 is substituted with Tyr or Phe.

16. The nucleic acid molecule of claim 15, wherein the amino acid at position 172 is substituted with Ser.

17. The nucleic acid molecule of claim 14, wherein the first amino acid sequence further comprises a substitution at position 152.

18. The nucleic acid molecule of claim 17, wherein the amino acid at position 152 is substituted with Phe.

19. The nucleic acid molecule of claim 1 or 2, wherein F is an immunoglobulin-derived domain.

20. The nucleic acid of claim 19, wherein the immunoglobulin-derived domain is selected from the group consisting of the Fc domain of IgG or the heavy chain of IgG.

21. An IL-4/13-binding fusion polypeptide encoded by the nucleic acid molecule of claim 1 or 2.

22. A multimeric protein comprising two or more of the fusion polypeptides of claim 21.

23. A vector comprising the nucleic acid molecule of claim 1 or 2.

24. A vector system comprising the vector of claim 23, in an isolated host cell.

25. A method of producing a fusion polypeptide, comprising culturing the host cell of claim 24 under conditions suitable for expression of the protein from the host cell, and recovering the polypeptide so produced.

26. A fusion polypeptide $(R1)_x$-$(R2)_y$-F, wherein

R1 is an interleukin-4 receptor α (IL-4Rα) component comprising a first amino acid sequence of amino acid residues 1-231 of SEQ ID NO:2, wherein one or more amino acids at positions 67, 68, 71, 152, 164, 171, 172, 175 and 198 are modified;

R2 is an interleukin-13 receptor α1 (IL-13Rα1) component comprising a second amino acid sequence of amino acid residues 27-343 of SEQ ID NO:3, wherein said second amino acid sequence may comprise one to three modifications;

F is a multimerizing component; and x and y are each independently a positive integer $\geqq 1$.

27. The fusion polypeptide of claim 26, wherein the first amino acid sequence further comprises a modification at position 207.

* * * * *